(12) United States Patent
Nagase et al.

(10) Patent No.: US 8,124,807 B2
(45) Date of Patent: Feb. 28, 2012

(54) SULFONYL-SUBSTITUTED 6-MEMBERED RING DERIVATIVE

(75) Inventors: Tsuyoshi Nagase, Tokushima (JP); Takahide Sasaki, Kawasaki (JP); Toshiyuki Takahashi, Tsukuba (JP)

(73) Assignee: MSD K.K., Tokyo (JP)

( * ) Notice: Subject to any disclaimer, the term of this patent is extended or adjusted under 35 U.S.C. 154(b) by 70 days.

(21) Appl. No.: 12/745,761

(22) PCT Filed: Dec. 16, 2008

(86) PCT No.: PCT/JP2008/072811
§ 371 (c)(1),
(2), (4) Date: Jun. 2, 2010

(87) PCT Pub. No.: WO2009/081789
PCT Pub. Date: Jul. 2, 2009

(65) Prior Publication Data
US 2010/0249147 A1 Sep. 30, 2010

(30) Foreign Application Priority Data
Dec. 26, 2007 (JP) .................... 2007-334073

(51) Int. Cl.
C07C 233/10 (2006.01)
C07D 213/62 (2006.01)
C07D 239/38 (2006.01)

(52) U.S. Cl. ....................................... 564/162

(58) Field of Classification Search .......... None
See application file for complete search history.

(56) References Cited

U.S. PATENT DOCUMENTS

2007/0208001 A1* 9/2007 Zhuo et al. ............ 514/212.02
2010/0056597 A1 3/2010 Takahashi et al.

FOREIGN PATENT DOCUMENTS

| CA | 2 701 406 A1 | | 4/2009 |
|---|---|---|---|
| EP | 2 204 368 A1 | | 7/2010 |
| WO | WO 2006/087543 | * | 8/2006 |
| WO | 2009/099086 A1 | | 8/2009 |

OTHER PUBLICATIONS

Matsuzaka et al. in Nature Medicine 13 (10) 1193-1202, 2007.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Dorwald F. A. (Side reactions in organic synthesis, 2005, Wiley, VCH, Weinheim, p. IX of Preface.*

Lee, S. H. et al., "Fatty Acid Synthesis by Elongases in Trypanosomes", Cell, 2006, pp. 691-699, vol. 126.
Matsuzaka, T. et al., "Cloning and characterization of a mamalian fatty acyl-CoA elongase as a lipogenic enzyme regulated by SREBPs", Journal of Lipid Research, 2002, pp. 911-920, vol. 43.

* cited by examiner

Primary Examiner — Timothy Thomas
Assistant Examiner — Dennis Heyer
(74) Attorney, Agent, or Firm — Janet E. Fair; John C. Todaro

(57) ABSTRACT

[Problem]
To provide a compound that is useful as an agent in the prevention and treatment of circulatory system, nervous system, metabolic, reproductive system, and gastrointestinal diseases.

[Means for Resolution]
A compound or a pharmaceutically acceptable salt thereof represented by the following Formula (I):

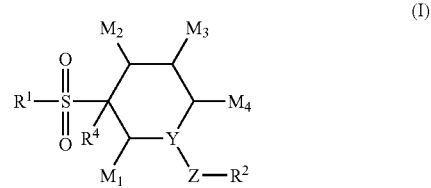

[wherein, Z represents formula (II-1), (II-2), or (II-3),

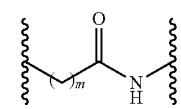

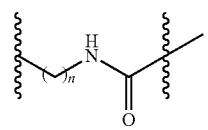

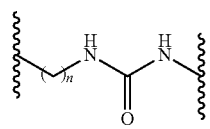

wherein m and n are 0, 1, or 2,
Y represents $CR^3$ or N, $R^1$ represents a $C_{1-6}$ alkyl, $C_{3-8}$ cycloalkyl, etc., $R^2$ represents phenyl or a heteroaryl, etc., $R^3$ and $R^4$ each independently represent a hydrogen atom, a $C_{1-6}$ alkyl, etc., $M_1$, $M_2$, $M_3$, and $M_4$ each independently represent a hydrogen atom, a $C_{1-6}$ alkyl, etc.]

4 Claims, No Drawings

US 8,124,807 B2

SULFONYL-SUBSTITUTED 6-MEMBERED RING DERIVATIVE

CROSS-REFERENCE TO RELATED APPLICATIONS

This application is a U.S. National Phase application under 35 U.S.C. §371 of PCT Application No. PCT/JP2008/072811, filed Dec. 16, 2008, which published as WO 2009/081789 A1 on Jul. 2, 2009, and claims priority under 35 U.S.C. §365(b) from Japanese patent application No. JP2007-334073, filed Dec. 26, 2007.

TECHNICAL FIELD

The present invention is useful in the field of medicine. More precisely, the sulfonyl-substituted 6-membered ring derivative of the invention acts as a long-chain fatty acyl elongase (hereinafter this may be abbreviated as LCE) inhibitor and is useful for preventives or remedies for various circulation system disorders, nervous system disorders, metabolic disorders, reproduction system disorders, digestive system disorders, neoplasm, infectious diseases, etc., or for herbicides.

BACKGROUND ART

Obesity is a condition of having a significantly greater body weight than an average body weight as a result of accumulation of neutral fat in fat cells due to continuous excess energy intake compared with energy consumption (Eiji Itagaki, "STEP series, Metabolism, Endocrinology", Kaiba Shobo, 1st Ed., 1998, p. 105). It is known that the excessively-accumulated fat causes, for example, insulin resistance, diabetes, hypertension, hyperlipidemia, etc., and that a plurality of those factors as combined much increase a risk of onset of atherosclerosis; and the condition is referred to as a metabolic syndrome. Further, it is known that hypertriglyceridemia or obesity increases a risk of, for example, pancreatitis, hepatic dysfunction, cancer such as breast cancer, uterine cancer, ovarian cancer, colon cancer, prostate cancer, etc., menstrual abnormality, arthritis, gout, cholecystitis, gastroesophageal reflux, obesity hypoventilation syndrome (Pickwickian syndrome), sleep apnea syndrome, etc. It is widely known that diabetes often leads to onset of, for example, angina pectoris, heat failure, stroke, claudication, retinopathy, reduced vision, renal failure, neuropathy, skin ulcer, infection, etc. [The Merck Manual of Medical Information, Domestic 2nd Ed., Merck & Co., 2003].

LCE is an enzyme existing in the endoplasmic reticula of cells, and is a type of an enzyme group that catalyzes the carbon chain elongation reaction of a fatty acid having at least 12 carbon atoms, specifically catalyzing the rate-determining condensation step of the reaction. In mammals, many fatty acids newly synthesized in the living bodies have a chain length of from 16 to 18 carbon atoms. These long-chain fatty acids constitute more than 90% of all the fatty acids existing in cells. These are important components of cell membranes, and are the essential ingredients of the fatty tissue that is the largest energy storage organ in animals. New fatty acid synthesis occurs most frequently in liver, and through the synthesis, the excessive glucose in a living body is converted into a fatty acid. Glucose is converted into a pyruvic acid salt through glycolysis, and the pyruvic acid salt is converted into a citric acid salt by mitochondria and then transferred to a cytosol. ATP citrate lyase in the cytosol produces an acetyl CoA that is a precursor of fatty acid and cholesterol. The acetyl CoA is carboxylated by an acetyl CoA carboxylate (ACC) to form a malonyl CoA. A multifunctional enzyme, fatty acid synthase (FAS) elongates a fatty acid by two carbons, using malonyl CoA, acetyl CoA and NADPH. In rodents, the main final product of FAS is palmitoyl CoA having 16 carbon atoms, and the carbon chain of the palmitoyl CoA is elongated by 2 carbons by LCE [Journal of Biological Chemistry, 276 (48), 45358-45366, (2001)]. It is known that excessive fatty acid synthesis promotion in living bodies increases neutral fat, etc., and finally causes fat accumulation. For example, WO2005/005665 (Patent Reference 1) shows a direct relationship between LCE and obesity. In addition, there is a report indicating the change in the expression level of mouse FACE (LCE) by eating (Matsuzaka T., et al., J. Lipid Res., 43(6): 911-920 (2002); Non-Patent Reference 1).

It is known that LCE exists also in protozoans and nematodes and participates in cell growth. For example, it is said that, in *Trypanosoma* protozoans that cause African trypanosomiasis (African sleeping sickness), a long-chain fatty acid is produced in a fatty acyl elongation route including LCE, and the intercellular fatty acyl elongation reaction inhibition may have some influence on the proliferation of *Trypanosoma* protozoans (Lee S. H., et al., Cell, 126: 691-699 (2006); Non-Patent Reference 2).

Any compound having an LCE inhibitory effect is heretofore not known at all. On the other hand, the compounds of the invention are derivatives having a sulfonyl on the saturated 6-membered ring thereof; however, compounds having an aryl or a heteroaryl bonding to the 3-position of a substituted sulfonyl saturated 6-membered ring via an amide bond or an urea bond therebetween are heretofore unknown.

Non-Patent Reference 1: J. Lipid Res., 43(6): 911-920 (2002)

Non-Patent Reference 2: Cell, 126: 691-699 (2006)

DISCLOSURE OF THE INVENTION

Problems that the Invention is to Solve

An object of the invention is to provide novel compounds having an LCE inhibitory effect.

Means for Solving the Problems

The present inventors have assiduously studied and, as a result, have found that a compound having a phenyl or a heteroaryl bonding to the 3-position of a sulfonyl-substituted cyclohexane ring or to the 1-position of a sulfonyl-substituted piperidine ring via an amide bond or an urea bond therebetween has an excellent LCE inhibitory effect, and have completed the present invention.

Specifically, the invention provides the following:

(1) A compound of a formula (I) or a pharmaceutically-acceptable salt thereof (hereinafter referred to as "compound of the invention"):

[Chemical Formula 1]

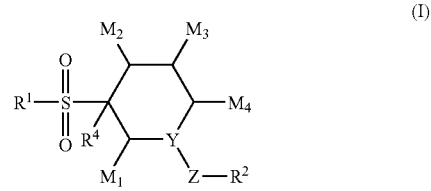

[wherein,

Z is selected from a group consisting of the following formulae (II-1), (II-2) and (II-3):

[Chemical Formula 2]

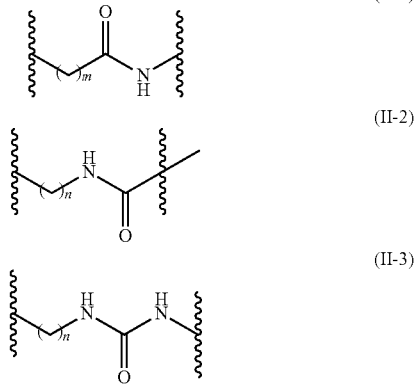

m and n each indicate 0, 1 or 2;

Y represents $CR^3$ or N, provided that when Y is N, then in (II-2) and (II-3), n is 0 or 2;

$R^1$ represents a $C_{1-6}$ alkyl, a $C_{3-8}$ cycloalkyl, an aryl or a heteroaryl, and wherein the alkyl, the cycloalkyl, the aryl or the heteroaryl may be substituted with a substituent selected from a group consisting of a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy and a heteroaralkyloxy;

$R^2$ represents a phenyl or a heteroaryl, and wherein the phenyl or the heteroaryl may be substituted with a substituent selected from a group consisting of a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy and a heteroaralkyloxy;

$R^3$ and $R^4$ each independently represent a hydrogen atom, a $C_{1-6}$ alkyl, a $C_{3-8}$ cycloalkyl, an aralkyl, a heteroaralkyl, an aryl or a heteroaryl, and wherein the alkyl, the cycloalkyl, the aralkyl, the heteroaralkyl, the aryl or the heteroaryl may be substituted with a substituent selected from a group consisting of a halogen, a $C_{1-6}$ alkyl, a halo-$C_{1-6}$ alkyl, a $C_{1-6}$ alkoxy and a halo-$C_{1-6}$ alkoxy;

$M_1$, $M_2$, $M_3$ and $M_4$ each independently represent a hydrogen atom, or a $C_{1-6}$ alkyl optionally substituted with a halogen; or $M_1$, taken together with $M_2$, $M_3$ or $M_4$, forms —$CH_2$— or —$CH_2$—$CH_2$—, or $M_4$, taken together with $M_2$, forms —$CH_2$— or —$CH_2$—$CH_2$—].

The invention also provides the following:

(2) A long-chain fatty acyl elongase (LCE) inhibitor comprising, as the active ingredient thereof, a compound of formula (I) or a pharmaceutically-acceptable salt thereof, (3) A pharmaceutical composition containing a compound of formula (I) or a pharmaceutically-acceptable salt thereof, (4) A preventive or a remedy for diabetes, obesity or non-alcoholic fatty liver, comprising, as the active ingredient thereof, a compound of formula (I) or a pharmaceutically-acceptable salt thereof.

In particular, the compounds of the invention have an LCE inhibitor effect, and are therefore useful as preventives and remedies for LCE-related various disorders, for example, circular system disorders such as hypertension, stenocardia, heart failure, myocardial infarction, stroke, claudication, diabetic nephropathy, diabetic retinopathy, reduced vision, electrolytic abnormality, atherosclerosis, etc.; central nervous system disorders such as bulimia, diabetic neuropathy, etc.; metabolic disorders such as metabolic syndrome, obesity, diabetes, insulin resistance, hyperlipidemia, hypercholesterolemia, hypertriglyceridemia, dyslipidemia, non-alcoholic fatty liver, hormone secretion abnormality, gout, fatty liver, etc.; reproduction system disorders such as menstrual abnormality, sexual dysfunction, etc.; digestive system disorders such as hepatic dysfunction, pancreatitis, cholecystitis, gastroesophageal reflux, etc.; respiratory system disorders such as obesity hypoventilation syndrome (Pickwickian syndrome), sleep apnea syndrome, etc.; infectious disorders caused by bacteria, fungi, parasites; malignant neoplasm; inflammatory disorders such as arthritis, skin ulcer, etc., and also as herbicides.

The meanings of the terms used in this description are described below, and the invention is described in more detail.

"Halogen" means a fluorine atom, a chlorine atom, a bromine atom, an iodine atom.

"$C_{1-6}$ alkyl" means a linear or branched alkyl having from 1 to 6 carbon atoms, including, for example, methyl, ethyl, propyl, isopropyl, butyl, isobutyl, sec-butyl, tert-butyl, pentyl, isopentyl, hexyl, isohexyl, etc.

"Halo-$C_{1-6}$ alkyl" means a $C_{1-6}$ alkyl substituted with one or more, preferably from 1 to 3, the same or different, above-mentioned halogen atoms at the substitutable position thereof, and includes, for example, fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl, etc.

"$C_{3-8}$ cycloalkyl" means a cycloalkyl having from 3 to 8 carbon atoms, including, for example, cyclopropyl, cyclobutyl, cyclopentyl, cyclohexyl, etc.

The above-mentioned "alkyl", "haloalkyl" or "cycloalkyl" may be optionally substituted with a substituent selected from a group consisting of a halogen, a cyano, a nitro, an oxo, —$OR^5$, —$R^5$, —$COR^5$, —$CO_2R^5$, —$NR^6R^7$, —$SR^5$, —$SOR^5$, —$SO_2R^5$, —$CONR^6R^7$, —$NR^5COR^6$, —$NR^5CO_2R^6$, —$OCONR^6R^7$, —$NR^5SO_2R^6$, —$SO_2NR^6R^7$ and —$NR^5CONR^6R^7$; and $R^5$, $R^6$ and $R^7$ are the same or different, each representing a hydrogen, a $C_{1-6}$ alkyl, a $C_{3-8}$ cycloalkyl, an aryl, a heterocyclyl or a heteroaryl; or $R^6$ and $R^7$, taken together with the nitrogen atom to which they bond, may form a heterocyclyl.

"$C_{1-6}$ alkoxy" means a linear or branched alkoxy having from 1 to 6 carbon atoms, including, for example, methoxy, ethoxy, propoxy, isopropoxy, butoxy, sec-butoxy, isobutoxy, tert-butoxy, pentyloxy, isopentyloxy, hexyloxy, isohexyloxy, etc.

"Halo-$C_{1-6}$ alkoxy" means a $C_{1-6}$ alkoxy substituted with one or more, preferably from 1 to 3, the same or different, above-mentioned halogen atoms at the substitutable position thereof, and includes, for example, fluoromethoxy, difluoromethoxy, trifluoromethoxy, 2-fluoroethoxy, 1,2-difluoroethoxy, chloromethoxy, 2-chloroethoxy, 1,2-dichloroethoxy, bromoethoxy, iodomethoxy, etc.

"$C_{1-6}$ alkoxycarbonyl" means a carbonyl with a $C_{1-6}$ alkoxy bonding thereto, and includes, for example, methoxycarbonyl, ethoxycarbonyl, n-propyloxycarbonyl, etc.

"$C_{1-6}$ alkoxycarbonylamino" means an amino group (—$NH_2$) in which one hydrogen atom is substituted with a $C_{1-6}$ alkoxycarbonyl, and includes, for example, methoxycarbonylamino, ethoxycarbonylamino, n-propyloxycarbonylamino, etc.

"$C_{1-6}$ alkylcarbonyl" means a carbonyl with a $C_{1-6}$ alkyl bonding thereto, and includes, for example, acetyl, propionyl, isobutyryl, valeryl, isovaleryl, pivaloyl, etc.

"$C_{1-6}$ alkylcarbonylamino" means an amino group in which one hydrogen atom is substituted with the above-mentioned $C_{1-6}$ alkylcarbonyl, and includes, for example, acetylamino, propionylamino, isobutyrylamino, valerylamino, isovalerylamino, pivaloylamino, etc.

"$C_{1-6}$ alkylsulfonyl" means a carbonyl with a $C_{1-6}$ alkyl bonding thereto, and includes, for example, methylsulfonyl, ethylsulfonyl, n-propylsulfonyl, etc.

"$C_{1-6}$ alkylsulfonylamino" means an amino group in which one hydrogen atom is substituted with a $C_{1-6}$ alkylsulfonyl, and includes, for example, methylsulfonylamino, ethylsulfonylamino, n-propylsulfonylamino, etc.

"$C_{1-6}$ alkylsulfinyl" means a sulfinyl with a $C_{1-6}$ alkyl bonding thereto, and includes, for example, methylsulfinyl, ethylsulfinyl, n-propylsulfinyl, etc.

"Aryl" includes, for example, phenyl, naphthyl, etc.

"Heteroaryl" means a 5-membered or 6-membered monocyclic heteroaryl having one or more, preferably from 1 to 3, the same or different hetero atoms selected from a group consisting of an oxygen atom, a nitrogen atom and a sulfur atom; or a condensed cyclic heteroaryl formed through condensation of above monocyclic heteroaryl and the above-mentioned aryl, or through condensation of the same or different such monocyclic heteroaryl groups; and it includes, for example, pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzimidazolyl, benzopyrazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl, pteridinyl, pyrido[3,2-b]pyridyl.

The above-mentioned "aryl" and "heteroaryl" may be substituted with, for example, a substituent selected from a group consisting of a hydroxy, a cyano, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, a $C_{3-8}$ cycloalkoxy, an amino, a $C_{1-6}$ alkylamino, a di-$C_{1-6}$ alkylamino, a halo-$C_{1-6}$ alkylamino, a di-halo-$C_{1-6}$ alkylamino, a $C_{3-8}$ cycloalkylamino, a di-$C_{3-8}$ cycloalkylamino, a carbamoyl, a $C_{1-6}$ alkylcarbamoyl, a di-$C_{1-6}$ alkylcarbamoyl, a halo-$C_{1-6}$ alkylcarbamoyl, a di-halo-$C_{1-6}$ alkylcarbamoyl, a $C_{3-8}$ cycloalkylcarbamoyl, a di-$C_{3-8}$ cycloalkylcarbamoyl, a thiol, a $C_{1-6}$ alkylthio, a halo-$C_{1-6}$ alkylthio, a $C_{3-8}$ cycloalkylthio, a $C_{1-6}$ alkylsulfinyl, a halo-$C_{1-6}$ alkylsulfinyl, a $C_{3-8}$ cycloalkylsulfinyl, a $C_{1-6}$ alkylsulfonyl a halo-$C_{1-6}$ alkylsulfonyl, a $C_{3-8}$ cycloalkylsulfonyl, a $C_{1-6}$ alkylcarbonyl, a halo-$C_{1-6}$ alkylcarbonyl, a $C_{3-8}$ cycloalkylcarbonyl, a $C_{1-6}$ alkoxycarbonyl, a halo-$C_{1-6}$ alkoxycarbonyl, a $C_{3-8}$ cycloalkoxycarbonyl, a $C_{1-6}$ alkoxycarbonylamino, a halo-$C_{1-6}$ alkoxycarbonylamino, a $C_{3-8}$ cycloalkoxycarbonylamino, a $C_{1-6}$ alkylcarbonylamino, a halo-$C_{1-6}$ alkylcarbonylamino and a $C_{3-8}$ cycloalkylcarbonylamino.

"Arylcarbonyl" means a group of carbonyl with the above-mentioned aryl bonding thereto.

"Heteroarylcarbonyl" means a group of carbonyl with the above-mentioned heteroaryl bonding thereto.

"Arylcarbonylamino" means an amino group in which one hydrogen atom is substituted with the above-mentioned arylcarbonyl.

"Heteroarylcarbonylamino" means an amino group in which one hydrogen atom is substituted with the above-mentioned heteroarylcarbonyl.

"Aryloxy" means a group of an oxygen atom with the above-mentioned aryl bonding thereto.

"Heteroaryloxy" means a group of an oxygen atom with the above-mentioned heteroaryl bonding thereto.

"Aryloxycarbonyl" means a group of carbonyl with the above-mentioned aryloxy bonding thereto.

"Heteroaryloxycarbonyl" means a group of carbonyl with the above-mentioned heteroaryloxy bonding thereto.

"Aryloxycarbonylamino" means an amino group in which one hydrogen atom is substituted with the above-mentioned aryloxycarbonyl.

"Heteroaryloxycarbonyl amino" means an amino group in which one hydrogen atom is substituted with the above-mentioned heteroaryloxycarbonyl.

"Arylsulfinyl" means a group of sulfinyl with the above-mentioned aryl bonding thereto.

"Heteroarylsulfinyl" means a group of sulfinyl with the above-mentioned heteroaryl bonding thereto.

"Arylsulfonyl" means a group of sulfonyl with the above-mentioned aryl bonding thereto.

"Heteroarylsulfonyl" means a group of sulfonyl with the above-mentioned heteroaryl bonding thereto.

"Arylsulfonylamino" means an amino group in which one hydrogen atom is substituted with the above-mentioned arylsulfonyl.

"Heteroarylsulfonylamino" means an amino group in which one hydrogen atom is substituted with the above-mentioned heteroarylsulfonyl.

"Aralkyl" means a group of the above-mentioned aryl with a $C_{1-6}$ alkyl bonding thereto, and includes benzyl, 1-phenylethyl, 2-phenylethyl, 1-naphthylmethyl, 2-naphthylmethyl, etc.

"Heteroaralkyl" means a group of the above-mentioned heteroaryl with the above-mentioned $C_{1-6}$ alkyl bonding thereto.

"Aralkyloxy" means a group of an oxygen atom with the above-mentioned aralkyl bonding thereto.

"Heteroaralkyloxy" means a group of an oxygen atom with the above-mentioned heteroaralkyl bonding thereto.

"Heterocyclyl" means a saturated, partially saturated or unsaturated, monocyclic or bicyclic ring containing from 4 to 10 carbon atoms and having 1, 2 or 3 hetero atoms selected from nitrogen, oxygen and sulfur atoms, in which the ring nitrogen atom may be substituted with a group selected from a C1-6 alkyl, amino-C1-6 alkyl, aryl, aryl-C1-6 alkyl and acyl, and the ring carbon atom may be substituted with a C1-6 alkyl, an amino-C1-6 alkyl, an aryl, an aryl-C1-6 alkyl, a heteroaryl, a C1-6 alkoxy, a hydroxy or an oxo, and includes, for example, pyrrolidinyl, oxazolidinyl, thiazolidinyl, piperidinyl, morpholinyl, piperazinyl, dioxolanyl and tetrahydropyranyl.

"Salts" of the compounds of the invention mean ordinary, pharmaceutically-acceptable salts. For example, when the compounds have a carboxyl group, then they may form base-addition salts at the carboxyl group; or when the compounds have an amino group or a basic heterocyclic group, they may form acid-addition salts at the basic nitrogen-containing heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

"Substitutable position" is meant to indicate the position of a hydrogen atom chemically substitutable on the carbon, nitrogen, oxygen and/or sulfur atoms of the compound, and the substitution gives a chemically stable compound.

Depending on the type of the substituent therein and on the salt form thereof, the compound of the invention may include stereoisomers and tautomers such as optical isomers, diastereomers and geometric isomers; and the compound of the invention encompasses all such stereoisomers, tautomers and their mixtures.

The invention includes various crystals, amorphous substances, salts, hydrates and solvates of the compounds of the invention.

Further, prodrugs of the compounds of the invention are within the scope of the invention. In general, such prodrugs are functional derivatives of the compounds of the invention that can be readily converted into compounds that are needed by living bodies. Accordingly, in the method of treatment of various diseases in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985. Metabolites of these compounds include active compounds that are produced by putting the compounds of the invention in a biological environment, and are within the scope of the invention.

For concretely illustrating the compounds of the invention, the symbols used in formula (I) are described below with reference to their specific examples.

$R^1$ represents a $C_{1-6}$ alkyl, a $C_{3-8}$ cycloalkyl, an aryl or a heteroaryl, and wherein the alkyl, the cycloalkyl, the aryl or the heteroaryl may be substituted with a substituent selected from a group consisting of a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy and a heteroaralkyloxy.

$R^1$ is preferably a $C_{1-6}$ alkyl, a $C_{3-8}$ cycloalkyl, an aryl or a heteroaryl, and the group may be substituted with a substituent selected from a group consisting of a halogen, a $C_{1-6}$ alkyl, a halo-$C_{1-6}$ alkyl and a $C_{1-6}$ alkoxy.

Concretely, $R^1$ includes methyl, ethyl, propyl, isopropyl, butyl, isobutyl, cyclopropyl, cyclobutyl, cyclopentyl, cyclohexyl, phenyl, 2-chlorophenyl, 3-chlorophenyl, 4-chlorophenyl, 2-fluorophenyl, 3-fluorophenyl, 4-fluorophenyl, 2,3-difluorophenyl, 2,4-difluorophenyl, 2-trifluoromethylphenyl, 3-trifluoromethylphenyl, 4-trifluoromethylphenyl, 2-methoxyphenyl, 3-methoxyphenyl, 4-methoxyphenyl, pyridin-2-yl, pyridin-3-yl, pyridin-4-yl, pyrimidin-2-yl, pyrazin-2-yl, pyridazin-3-yl, 2-thienyl, 3-thienyl, 1-methyl-1H-imidazole-4-yl, 5-methyl-1,3,4-thiadiazol-2-yl, 1,3-thiazol-2-yl, 1,3-oxazol-2-yl, 1,3,4-thiadiazol-2-yl, etc.; and preferred are propyl, isopropyl, butyl, isobutyl, cyclopropyl, phenyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-methoxyphenyl, 3-methoxyphenyl, 4-methoxyphenyl, pyridin-2-yl, pyridin-3-yl, pyridin-4-yl, pyrimidin-2-yl, pyrazin-2-yl, pyridazin-3-yl, 2-thienyl, 3-thienyl, 1-methyl-1H-imidazol-4-yl, 5-methyl-1,3,4-thiadiazol-2-yl, 1,3-thiazol-2-yl, 1,3-oxazol-2-yl, 1,3,4-thiadiazol-2-yl.

$R^2$ represents a phenyl or a heteroaryl, wherein the phenyl or the heteroaryl may be substituted with a substituent selected from a group consisting of a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy and a heteroaralkyloxy.

$R^2$ is preferably a phenyl or an aryl, and the phenyl or the heteroaryl may be substituted with a substituent selected from a group consisting of a halogen, a $C_{1-6}$ alkyl, a halo-$C_{1-6}$ alkyl, a $C_{1-6}$ alkoxy, a $C_{3-6}$ cycloalkyl, an aryl, an aralkyl and an aralkyloxy.

Concretely, $R^2$ includes phenyl, 2-methoxyphenyl, 3-methoxyphenyl, 4-methoxyphenyl, 2-ethoxyphenyl, 3-ethoxyphenyl, 4-ethoxyphenyl, 2-isopropoxyphenyl, 3-isopropoxyphenyl, 4-isopropoxyphenyl, 2-isobutyloxyphenyl, 3-isobutyloxyphenyl, 4-isobutyloxyphenyl, 2-cyclopropyloxyphenyl, 3-cyclopropyloxyphenyl, 4-cyclopropyloxyphenyl, 2-fluorophenyl, 3-fluorophenyl, 4-fluorophenyl, 2-chlorophenyl, 3-chlorophenyl, 4-chlorophenyl, 2-trifluoromethylphenyl, 3-trifluoromethylphenyl, 4-trifluoromethylphenyl, 2-phenoxyphenyl, 3-phenoxyphenyl, 4-phenoxyphenyl, 2-benzyloxyphenyl, 3-benzyloxyphenyl, 4-benzyloxyphenyl, 2-benzylphenyl, 3-benzylphenyl, 4-benzylphenyl, 2-methylphenyl, 3-methylphenyl, 4-methylphenyl, 2-isopropylphenyl, 3-isopropylphenyl, 4-isopropylphenyl, 5-isopropylphenylpyridin-2-yl, 6-isopropoxyphenylpyridin-3-yl, 5-isopropoxypyrimidin-2-yl, 3-methoxypyridin-2-yl, 3-cyclopropyl-1H-pyrazol-5-yl, 5-isopropoxy-1H-pyrazol-3-yl, etc.; and preferred are phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2-isopropylphenyl, 3-isopropylphenyl, 4-isopropylphenyl, 2-isopropylphenyl, 3-isopropylphenyl, 4-isopropylphenyl, 2-isopropoxyphenyl, 3-isopropoxyphenyl, 4-isopropoxyphenyl, 2-benzylphenyl, 3-benzylphenyl, 4-benzylphenyl, 2-benzyloxyphenyl, 3-benzyloxyphenyl, 4-benzyloxyphenyl, 5-isopropoxyphenylpyridin-2-yl, 6-isopropoxyphenylpyridin-3-yl, 5-isopropoxypyrimidin-2-yl, 3-methoxypyridin-2-yl, 3-cyclopropyl-1H-pyrazol-5-yl, 5-isopropoxy-1H-pyrazol-3-yl.

Y represents $CR^3$ or N, and is preferably $CR^3$.

$R^3$ represents a hydrogen atom, a $C_{1-6}$ alkyl, an aralkyl, an aryl or a heteroaryl, and the alkyl, the aralkyl, the aryl or the heteroaryl may be substituted with a substituent selected from a group consisting of a halogen, a $C_{1-6}$ alkyl, a halo-$C_{1-6}$ alkyl, a $C_{1-6}$ alkoxy and a halo-$C_{1-6}$ alkoxy.

Concretely, $R^3$ includes a hydrogen atom, methyl, ethyl, propyl, butyl, pentyl, hexyl, isopropyl, isobutyl, isopentyl, phenyl, pyridin-2-yl, pyridin-3-yl, pyridin-4-yl, pyrimidin-2-yl, benzyl, etc.; and preferred are a hydrogen atom, methyl, ethyl, propyl, isopropyl, phenyl, pyridin-2-yl, pyridin-3-yl, pyridin-4-yl, benzyl.

$R^4$ has the same meaning as that of $R^3$.

$R^4$ is preferably a hydrogen atom.

Z is selected from the following formulae (II-1), (II-2) and (II-3).

[Chemical Formula 3]

(II-1)

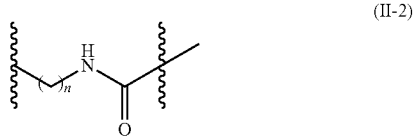
(II-2)

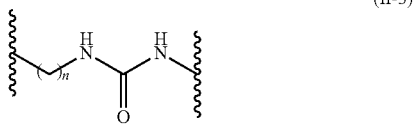
(II-3)

[In the formulae, m and n each indicate 0, 1 or 2, and when Y is N, then n is 0 or 2.]

m is preferably 0 or 1.

n is preferably 0 or 1. When Y is N, then n is preferably 0.

Z is more preferably a formula (II-1) or (II-2), even more preferably (II-1).

$M_1$, $M_2$, $M_3$ and $M_4$ each independently represent a hydrogen atom, or a $C_{1-6}$ alkyl optionally substituted with a halogen; or $M_1$, taken together with $M_2$, $M_3$ or $M_4$, forms —$CH_2$— or —$CH_2$—$CH_2$—, or $M_4$, taken together with $M_2$, forms —$CH_2$— or —$CH_2$—$CH_2$—.

Concretely, $M_1$, $M_2$, $M_3$ and $M_4$ are each independently a hydrogen atom, methyl, ethyl, n-propyl, n-butyl, chloromethyl, fluoromethyl, trifluoromethyl, etc.; or $M_1$, as taken together with $M_2$, $M_3$ or $M_4$, forms —$CH_2$— or —$CH_2$—$CH_2$—, or $M_4$, as taken together with $M_2$, forms —$CH_2$— or —$CH_2$—$CH_2$—.

Concrete combinations of $M_1$, $M_2$, $M_3$ and $M_4$ are as follows:

1) $M_1$, taken together with $M_2$, forms —$CH_2$— or —$CH_2$—$CH_2$—, and $M_3$ and $M_4$ are each independently a hydrogen atom or a $C_{1-6}$ alkyl optionally substituted with a halogen;

2) $M_1$, taken together with $M_3$, forms —$CH_2$— or —$CH_2$—$CH_2$—, and $M_2$ and $M_4$ are each independently a hydrogen atom or a $C_{1-6}$ alkyl optionally substituted with a halogen;

3) $M_1$, taken together with $M_4$, forms —$CH_2$— or —$CH_2$—$CH_2$—, and $M_2$ and $M_3$ are each independently a hydrogen atom or a $C_{1-6}$ alkyl optionally substituted with a halogen;

4) $M_4$, taken together with $M_2$, forms —$CH_2$— or —$CH_2$—$CH_2$—, and $M_1$ and $M_3$ are each independently a hydrogen atom or a $C_{1-6}$ alkyl optionally substituted with a halogen;

5) $M_1$, $M_2$, $M_3$ and $M_4$ are all hydrogen atoms,

6) One of $M_1$, $M_2$, $M_3$ and $M_4$ is a $C_{1-6}$ alkyl optionally substituted with a halogen, and the others are hydrogen atoms.

7) Two of $M_1$, $M_2$, $M_3$ and $M_4$ each are a $C_{1-6}$ alkyl optionally substituted with a halogen, and the others are hydrogen atoms.

More preferred is a case where $M_1$, $M_2$, $M_3$ and $M_4$ are all hydrogen atoms.

Concretely, the compounds of formula (I) include the following:

(1R*,3R*)-N-(4-isopropoxyphenyl)-3-(phenylsulfonyl)cyclohexanecarboxamide, (1R*,3S*)-N-(4-isopropoxyphenyl)-3-(phenylsulfonyl)cyclohexanecarboxamide, (1R*,3R*)-N-(4-isopropoxyphenyl)-3-(pyridin-2-ylsulfonyl)cyclohexanecarboxamide, (1R*,3R*)-N-(4-isopropoxyphenyl)-3-(pyrimidin-2-ylsulfonyl)cyclohexanecarboxamide, (1R*,3R*)-N-(4-isopropoxyphenyl)-3-(1,3-thiazol-2-ylsulfonyl)cyclohexanecarboxamide, (1R*,3R*)-N-(4-isopropoxyphenyl)-3-(1,3,4-thiadiazol-2-ylsulfonyl)cyclohexanecarboxamide, (1R*,3R*)-N-(4-isopropoxyphenyl)-3-[(1-methyl-1H-imidazol-2-yl)sulfonyl]cyclohexanecarboxamide, (1R*,3R*)-N-(5-isopropoxypyridin-2-yl)-3-(phenylsulfonyl)cyclohexanecarboxamide, (1R*,3R*)-N-(5-isopropoxypyridin-2-yl)-3-(pyridin-2-ylsulfonyl)cyclohexanecarboxamide, (1R*,3R*)-N-(5-isopropoxypyridin-2-yl)-3-(pyridin-4-ylsulfonyl)cyclohexanecarboxamide, (1R*,3R*)-N-(5-isopropoxypyridin-2-yl)-3-(pyrimidin-2-ylsulfonyl)cyclohexanecarboxamide, (1R*,3R*)-N-(5-isopropoxypyridin-2-yl)-3-(1,3-thiazol-2-ylsulfonyl)cyclohexanecarboxamide, (1R*,3R*)-3-(butylsulfonyl)-N-(5-isopropoxypyridin-2-yl)cyclohexanecarboxamide, (1R*,3R*)-N-(5-isopropoxypyridin-2-yl)-3-(pyrazin-2-ylsulfonyl)cyclohexanecarboxamide, (1R*,3R*)-N-(3-isopropoxy-1H-pyrazol-5-yl)-3-(pyridin-2-ylsulfonyl)cyclohexanecarboxamide, (1R*,3S*)-N-(3-isopropoxy-1H-pyrazol-5-yl)-3-(pyridin-2-ylsulfonyl)cyclohexanecarboxamide, N-(4-isopropoxyphenyl)-3-(phenylsulfonyl)piperidine-1-carboxamide.

Preferred are the following:

(1R*,3R*)-N-(5-isopropoxypyridin-2-yl)-3-(phenylsulfonyl)cyclohexanecarboxamide, (1R*,3R*)-N-(5-isopropoxypyridin-2-yl)-3-(pyridin-2-ylsulfonyl)cyclohexanecarboxamide, (1R*,3R*)-N-(5-isopropoxypyridin-2-yl)-3-(pyrimidin-2-ylsulfonyl)cyclohexanecarboxamide, (1R*,3R*)-N-(5-isopropoxypyridin-2-yl)-3-(1,3-thiazol-2-ylsulfonyl)cyclohexanecarboxamide, (1R*,3R*)-N-(3-isopropoxy-1H-pyrazol-5-yl)-3-(pyridin-2-ylsulfonyl)cyclohexanecarboxamide.

Production Methods for Compounds of Formula (I)

The compounds of the invention can be produced, for example, according to the production methods mentioned below or according to the methods shown in Examples. However, the production methods for the compounds of the invention are not limited to these examples.

Production Method 1:

The compounds of formula (I-1) can be produced according to the following method.

Production Method 1

[Chemical Formula 4]

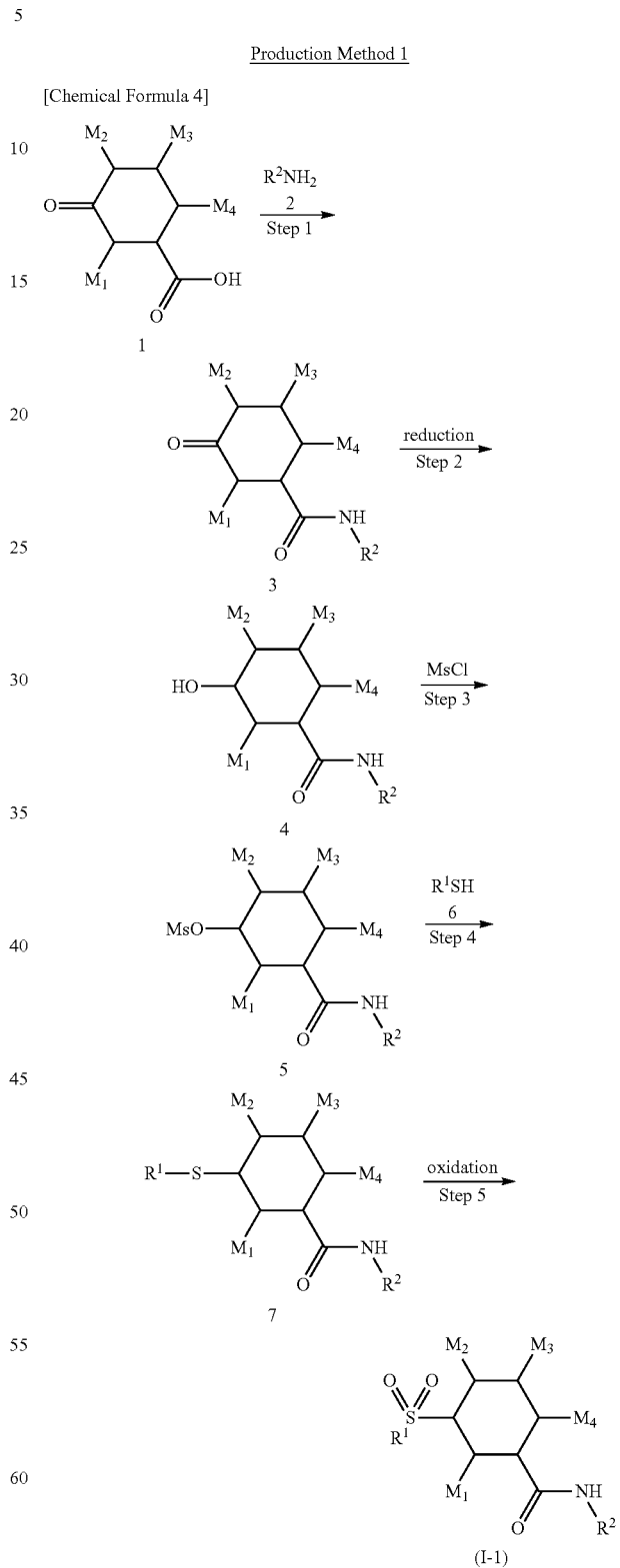

[In the formulae, the symbols have the same meanings as above.]

Step 1:

A compound 1 is amidated with a compound 2 in an organic solvent to give a compound 3.

The amidation may be attained in any known conventional method. For example, there are mentioned a method of reacting the compound 1 and the compound 2 in the presence of a condensing agent; and a method of activating the carboxylic acid moiety of the compound 1 in a known method to give a reactive derivative followed by amidating the derivative with the compound 2. (For both methods, referred to is "Basis and Experiments of Peptide Synthesis" (Nobuo Izumiya, Maruzen, 1983).)

For example, the method of using a condensing agent is as follows.

Briefly, the compound 1 and the compound 2 are condensed in a reaction solvent, using a condensing agent, thereby giving the compound 3.

The amount of the compound 2 to be used may be from 1 to 3 mols per mol of the compound 1.

The condensing agent includes dicyclohexylcarbodiimide, 1-ethyl-3-(3-dimethylaminopropyl)-carbodiimide, O-(7-azabenzotriazol-1-yl)-1,1,3,3-tetramethyluronium hexafluorophosphate (hereinafter referred to as "HATU"), etc.; and its amount to be used may be from 1 to 3 mols per mol of the compound 1.

For promoting the reaction, hydroxybenzotriazole (hereinafter referred to as "HOBT") may be added to the reaction system. The amount of HOBT to be used may be from 1 to 3 mols per mol of the compound 1.

The reaction solvent includes tetrahydrofuran (hereinafter referred to as "THF"), 1,4-dioxane, N,N-dimethylformamide (hereinafter referred to as "DMF"), dimethyl sulfoxide (hereinafter referred to as "DMSO"), dichloromethane, chloroform and their mixed solvents.

The reaction temperature may be from 0 to 100° C., preferably from 0 to 50° C., and in general, the reaction may complete within 1 to 24 hours.

The compound 3 produced according to the above-mentioned method may be readily isolated and purified in an ordinary separation method. The method includes, for example, solvent extraction, recrystallization, column chromatography, preparative thin-layer chromatography and the like (the same shall apply hereinunder).

The compound 1 includes 3-oxocyclohexanecarboxylic acid, etc.; and the compound 2 includes 3-isopropoxy-1H-pyrazole-5-amine, 4-isopropoxyaniline, etc.

Step 2:

The compound 3 is reduced in a reaction solvent in an ordinary method to give a compound 4.

The reduction method is not specifically defined. Using a reducing agent such as lithiumaluminium hydride, sodium borohydride or the like, the ketone moiety may be reduced in a conventional known method.

For example, when sodium borohydride is used, methanol, ethanol or the like is used as the reaction solvent, and the compound 3 is reduced with from 1 to 3 mols, per mol of the compound 3, of sodium borohydride at room temperature for 1 to 6 hours, thereby giving a compound 4.

Step 3:

The compound 4 is mesylated to give a compound 5. The mesylation method is not specifically defined. For example, mesyl chloride is used as a mesylating agent, as combined with triethylamine serving as a base.

Step 4:

The compound 5 is reacted with a compound 6 in a reaction solvent in the presence of a base to give a compound 7.

The amount of the compound 6 to be used may be from 1 to 10 mols per mol of the compound 5, preferably from 1 to 5 mols.

The base includes sodium carbonate, potassium carbonate, cesium carbonate, etc.

The amount of the base to be used may be from 1 to 10 mols pre mol of the compound 5, preferably from 1 to 5 mols.

The reaction solvent includes DMF, THF, 1,4-dioxane, etc.

The reaction temperature may be from 20 to 130° C., preferably from 20 to 100° C., and in general, the reaction may complete within 3 to 24 hours.

For promoting the reaction, potassium iodide may be added to the reaction liquid. The amount of potassium iodide to be used may be from 1 to 10 mols per mol of the compound 5, preferably from 1 to 5 mols.

The compound 6 includes thiophenol, 2-mercaptopyridine, 2-mercaptopyrimidine, 2-mercaptothiazole, etc.

Step 5:

The compound 7 is oxidized to give a compound of formula (I-1).

The oxidation method is not specifically defined. For example, m-chloroperbenzoic acid, potassium permanganate or the like may be used.

When m-chloroperbenzoic acid is used, the reaction is attained in a solvent such as methylene chloride, chloroform, etc.

The amount of m-chloroperbenzoic acid to be used may be from 2 to 5 mols per mol of the compound 7, and in general, the reaction may be attained at room temperature for 1 to 5 hours.

On the other hand, when potassium permanganate is used, the reaction may be attained in a mixed solvent of acetone/water. Acetic acid may be added to the reaction system.

The amount of potassium permanganate to be used may be from 2 to 6 mols per mol of the compound 7.

The amount of acetic acid to be used may be from 1 to 10 mols per mol of the compound 7.

The reaction temperature may be from 20 to 80° C., and in general, the reaction may complete within 1 to 24 hours.

Thus produced, the compound of formula (I-1) may be readily isolated and purified in an ordinary separation method. The method includes, for example, solvent extraction, recrystallization, column chromatography, preparative thin-layer chromatography, etc.

Production Method 2:

The production method 2 is an alternative production method for the compounds of formula (I-1) starting from a compound 1'.

Production Method 2

[Chemical Formula 5]

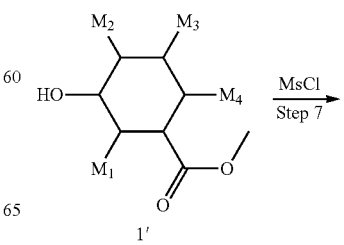

1'

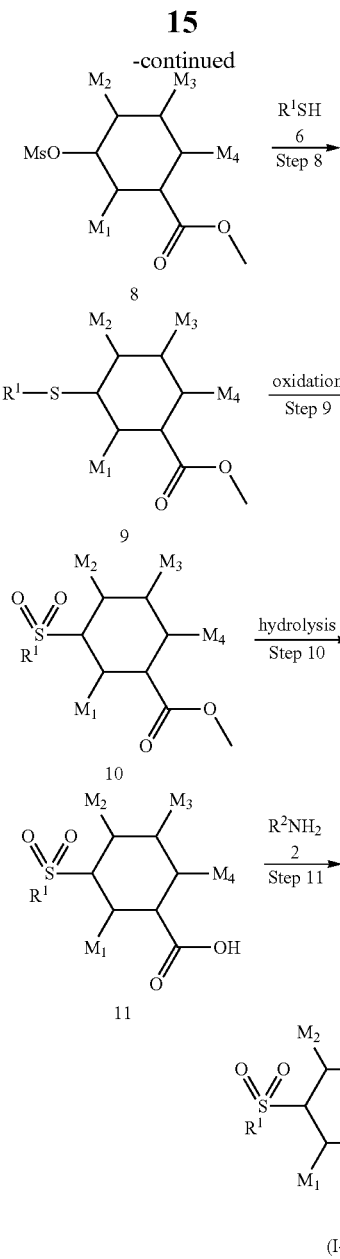

Step 11:

The compound 11 is reacted with a compound 2 in a reaction solvent to give a compound of formula (I-1). The reaction may be attained according to the step 1.

Production Method 3:

The production method 3 is for producing a compound of formula (I-1a):

Production Method 3

[Chemical Formula 6]

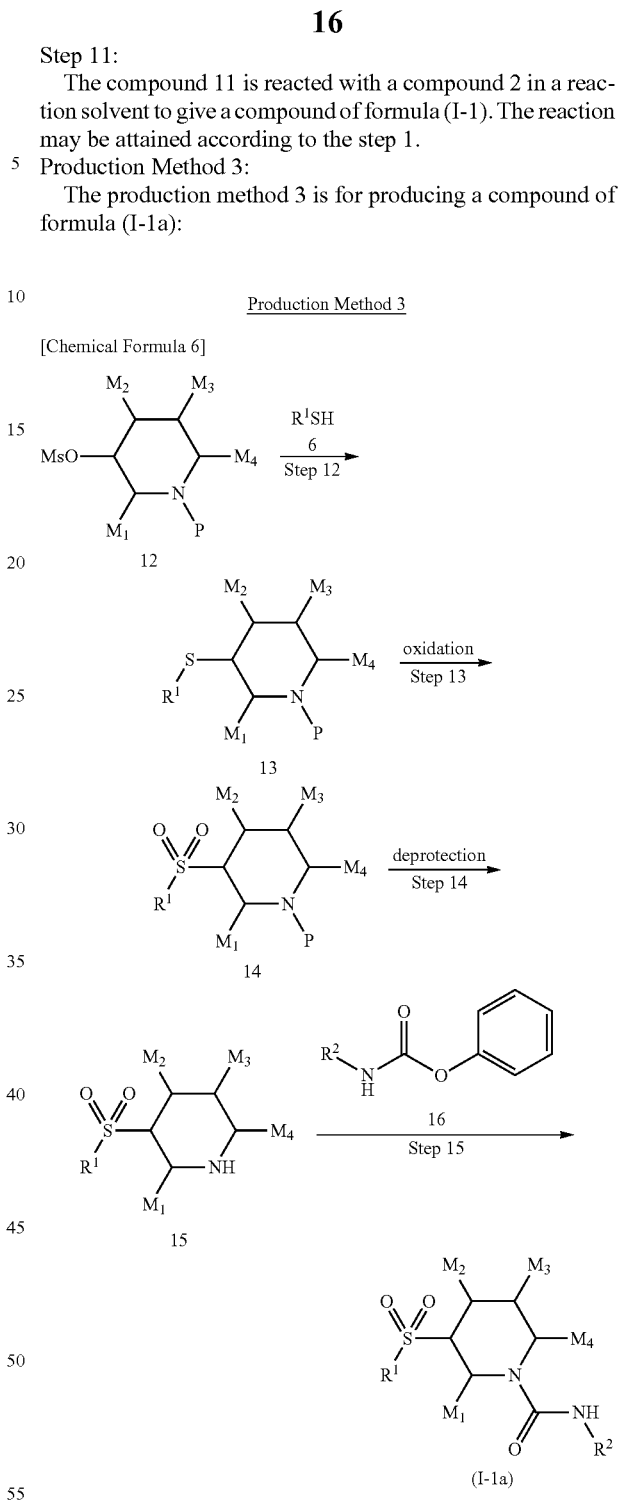

[In the formulae, P represents a protective group, and the other symbols have the same meanings as above.]

Step 12:

A compound 12 is reacted with a compound 6 in a reaction solvent to give a compound 13. The reaction may be attained according to the step 4.

The compound 12 includes benzyl 3-[(methylsulfonyl)oxy]piperidine-1-carboxylate.

Step 13:

The compound 13 is oxidized to give a compound 14. The oxidation may be attained according to the step 5.

[In the formulae, the symbols have the same meanings as above.]

Step 7:

A compound 1' is mesylated to give a compound 8. The mesylation may be attained according to the step 3.

Step 8:

The compound 8 is reacted with a compound 6 to give a compound 9. This reaction may be attained according to the step 4.

Step 9:

The compound 9 is oxidized to give a compound 10. The oxidation may be attained according to the step 5.

Step 10:

The ester of compound 10 is hydrolyzed to give a compound 11. The hydrolysis method is not specifically defined. For example, the ester may be hydrolyzed in an organic solvent of methanol, ethanol or the like, using an aqueous sodium hydroxide solution, an aqueous potassium hydroxide solution or the like, at a temperature of from room temperature to the boiling point of the solvent.

Step 14:

The amino-protective group in the compound 14 is deprotected to give a compound 15. The deprotection method may be attained according to the methods described in "Protective Groups in Organic Synthesis" (T. W. Green, John Wiley & Sons, 1981), or according to methods similar to them. The protective group includes tert-butyloxycarbonyl, benzyloxycarbonyl, p-methoxybenzyloxycarbonyl, etc.

For example, when a benzyloxycarbonyl group is used as the protective group, the compound 14 may be hydrogenated in the presence of palladium-carbon in a solvent such as methanol for deprotection of the group.

Step 15:

The compound 15 is reacted with a compound 16 in an organic solvent to give a compound of formula (I-1a).

The amount of the compound 16 to be used may be from 1 to 4 mols per mol of the compound 15, preferably from 1 to 2 mols.

The compound 16 includes phenyl (4-isopropoxyphenyl) carbamate, phenyl (2-methoxyphenyl)carbamate, etc.

The reaction solvent includes chloroform, methylene chloride, THF, 1,4-dioxane, etc.

The reaction temperature may be from 0 to 100° C., preferably from 0 to 80° C., and in general, the reaction may complete within 1 to 5 hours.

Production Method 4:

The production method 4 is for producing a compound of formula (I-2), starting from a compound 10.

Production Method 4

[Chemical Formula 7]

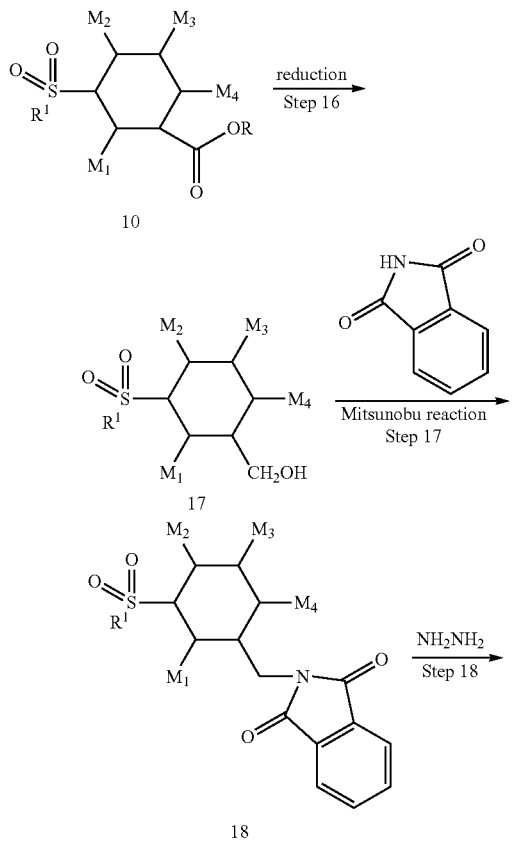

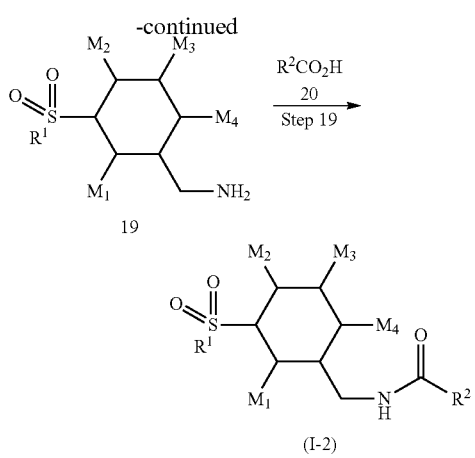

[In the formulae, the symbols have the same meanings as above.]

Step 16:

The ester moiety of a compound 10 is reduced to give a compound 17, according to a conventional known method using a reducing agent such as lithiumaluminium hydride, sodium borohydride, etc.

Step 17:

The compound 17 is condensed with phthalimide according to Mitsunobu reaction to give a compound 18.

Specifically, in a reaction solvent, the compound 17 is condensed with phthalimide in the presence of an azo compound such as dialkyl azodicarboxylate, 1,1'-(azodicarbonyl) diamide or the like and an organic phosphorus compound such as triaryl phosphine, trialkyl phosphine or the like, thereby giving a compound 18.

The azo compound includes dimethyl azodicarboxylate, diethyl azodicarboxylate, diisopropyl azodicarboxylate, 1,1'-(azodicarbonyl)dipiperidide, etc.; the triaryl phosphine includes triphenyl phosphine, tritolyl phosphine, etc.; the trialkyl phosphine includes triethyl phosphine, tributyl phosphine, etc. Above all, preferred is a combination of diisopropyl azodicarboxylate and triphenyl phosphine; or a combination of 1,1'-(azodicarbonyl)dipiperidide and tributyl phosphine.

The amount of phthalimide to be used may be from 1 to 10 mols per mol of the compound 17, preferably from 1 to 1.5 mols.

The amount of the azo compound and the organic phosphorus compound to be used may be from 1 to 3 mols, preferably from 1 to 1.5 mols of the azo compound per mol of the compound 17; and from 1 to 3 mols, preferably from 1 to 1.5 mols of the organic phosphorus compound per mol of phthalimide.

The reaction solvent includes carbon halides such as methylene chloride, chloroform, dichloroethane, carbon tetrachloride; aliphatic hydrocarbons such as n-heptane, n-hexane; aromatic hydrocarbons such as benzene, toluene, xylene; ethers such as diethyl ether, THF, dioxane, ethylene glycol dimethyl ether; esters such as methyl acetate, ethyl acetate; acetonitrile, N-methylpyrrolidone (hereinafter referred to as "NMP"), DMF, DMSO; and their mixed solvents, etc.

The reaction temperature may be from 0 to 100° C., preferably from 0 to 50° C., and in general, the reaction may complete within 2 to 24 hours.

Step 18:

The compound 18 is treated with hydrazine in a reaction solvent to give a compound 19.

The amount of hydrazine to be used may be from 1 to 10 mols per mol of the compound 18, preferably from 1 to 5 mols.

The reaction solvent includes methanol, ethanol, etc.

The reaction temperature may be from 0 to 60° C., preferably from 0 to 30° C., and in general, the reaction may complete within 1 to 24 hours.

Step 19:

The compound 19 is condensed with a compound 20 according to the step 1 to give a compound of formula (I-2).

The compound 20 includes 2-methoxybenzoic acid, 3-methoxybenzoic acid, 4-methoxybenzoic acid, 4-isopropoxybenzoic acid, etc.

The production method 5 is for producing a compound of formula (I-3):

Production Method 5

[Chemical Formula 8]

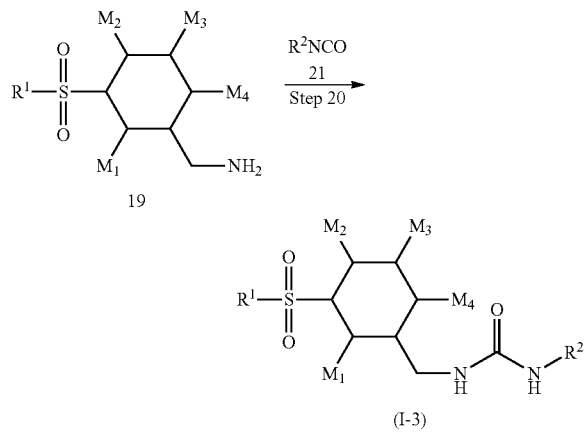

[In the formulae, the symbols have the same meanings as above.]

Step 20:

A compound 19 is reacted with a compound 21 in the presence of a base in a reaction solvent to give a compound of formula (I-3).

The compound 21 includes phenyl isocyanate, 4-methoxyphenyl isocyanate, etc.; and its amount to be used may be from 1 to 4 mols per mol of the compound 19, preferably from 1 to 2 mols.

The base includes triethylamine, diisopropylethylamine, pyridine, etc.; and the amount of the base to be used may be from 1 to 5 mols per mol of the compound 19, preferably from 1 to 3 mols.

The reaction solvent includes pyridine, THF, 1,4-dioxane, methylene chloride, chloroform, DMSO, etc.

The reaction temperature may be from 0 to 100° C., preferably from 0 to 50° C., and in general, the reaction may complete within 1 to 24 hours.

In the above reaction, when the reactants have amino, hydroxy, carboxy or the like not participating in the reaction, then the amino, hydroxy or carboxy may be suitably protected with a protective group, and the protective group may be removed after the reaction.

"Amino-protective group" includes, for example, an aralkyl such as benzyl, p-methoxybenzyl, 3,4-dimethoxybenzyl, o-nitrobenzyl, p-nitrobenzyl, benzhydryl, trityl; a $C_{1-6}$ alkanoyl such as formyl, acetyl, propionyl, butyryl, pivaloyl; benzoyl; an arylalkanoyl such as phenylacetyl, phenoxyacetyl; a $C_{1-6}$ alkoxycarbonyl such as methoxycarbonyl, ethoxycarbonyl, propyloxycarbonyl, tert-butoxycarbonyl; an aralkyloxycarbonyl such as benzyloxycarbonyl, p-nitrobenzyloxycarbonyl, phenethyloxycarbonyl; a $C_{1-6}$ alkylsilyl such as trimethylsilyl, tert-butyldimethylsilyl; and especially preferred are acetyl, pivaloyl, benzoyl, ethoxycarbonyl, tert-butoxycarbonyl, etc.

"Hydroxy-protective group" includes, for example, a substituted silyl such as trimethylsilyl, tert-butyldimethylsilyl (hereinafter this may be referred to as "TBDMS"), tert-butyldiphenylsilyl; a $C_{1-6}$ alkoxymethyl such as methoxymethyl, 2-methoxyethoxymethyl; tetrahydropyranyl; an aralkyl such as benzyl (hereinafter referred to as "Bn"), p-methoxybenzyl; an acyl such as formyl, acetyl; benzoyl, etc.

"Carboxyl-protective group" includes, for example, a $C_{1-6}$ alkyl such as methyl, ethyl, propyl, isopropyl, tert-butyl; a $C_{1-6}$ haloalkyl such as 2,2,2-trichloroethyl; a $C_{2-6}$ alkenyl such as 2-propenyl; an aralkyl such as benzyl, p-methoxybenzyl, p-nitrobenzyl, benzhydryl, trityl, etc.; and especially preferred are methyl, ethyl, tert-butyl, 2-propenyl, benzyl, p-methoxybenzyl, benzhydryl, etc.

The protective group may be introduced and removed according to the methods described in the above-mentioned reference, "Protective Groups in Organic Synthesis" or according to methods similar thereto.

The thus-produced compound of formula (I-1), (I-2) or (I-3) may be readily isolated and purified in an ordinary separation method. The method includes, for example, solvent extraction, recrystallization, column chromatography, preparative thin-layer chromatography and the like.

The compounds may be converted into a pharmaceutically-acceptable salts thereof in an ordinary manner; and on the contrary, their salts may also be converted into free compounds in an ordinary manner.

The usefulness of the compounds of the invention as medicines is proved, for example, by the following Pharmacological Test Example.

Pharmacological Test Example 1

LCE Enzyme Activity-Inhibitory Test

A test compound was dissolved in dimethyl sulfoxide (DMSO to be 10 mM), and then diluted with DMSO to prepare a 1000-fold concentrated solution of the test concentration. An improved Moon et al's method (J. Biol. Chem., Vol. 276, pp. 45358-45366, 2001) was employed for the LCE enzyme activity-inhibitor test. Concretely, the diluted compound was applied to a 96-well assay plate (Corning, 96-well assay block) in an amount of 1.0 µL/well; 50 µL of a phosphate buffer solution (100 mM potassium phosphate buffer, pH 6.5), and 25 µL of a substrate solution (100 mM potassium phosphate buffer (pH 6.5), 4.0 µM rotenone, 80 µM fatty acid-free bovine serum albumin, 160 µM palmitoyl CoA, 80 µM malonyl CoA, 3.5 µM [$^{14}$C]-malonyl CoA (1.92 GBq/mmol, by Amersham)) were added to each well; 25 µL of an enzyme solution (100 mM potassium phosphate buffer (pH 6.5), 100 µg/mL human LCE) was added thereto; the top of the plate was airtightly sealed up; and this was incubated with gently shaking and stirring at 37° C. for 90 minutes. Next, 100 µL of 5 N hydrochloric acid was added to each well, and the assay plate was stirred at room temperature for 5 minutes to stop the enzyme reaction with hydrolyzing the acyl CoA. Next, the enzyme reaction solution in each well was adsorbed by each well of a 96-well GF/C filter plate (Perkin Elmer Unifilter 96 GF/C); the individual wells were washed with water to remove the non-adsorbed malonyl CoA; and the GF/C filter plate was dried at 50° C. for 60 minutes. Next, 30 μL of a scintillator (Perkin Elmer Microscinti 0) was added to each well; then the top of the plate was sealed up; and the fixed [$^{14}$C] radioactivity was measured with a microplate scintillation counter (Perkin Elmer TopCount) to be the enzyme activity. The human LCE enzyme-inhibitory activity of the test compound was calculated, based on the radioactivity of the DMSO-added well with no test compound therein as a control. The activity of the compounds of the invention was analyzed according to the present assay, and the compounds inhibited the human LCE activity. The results are shown in Table 1.

TABLE 1

| Example No. | Compound | IC$_{50}$ (nM) |
|---|---|---|
| 2 | (1R*,3R*)-N-(4-isopropoxyphenyl)-3-(pyridin-2-ylsulfonyl)cyclohexanecarboxamide | 233 |
| 7 | (1R*,3R*)-N-(5-isopropoxypyridin-2-yl)-3-(phenylsulfonyl)cyclohexanecarboxamide | 30 |
| 8 | (1R*,3R*)-N-(5-isopropoxypyridin-2-yl)-3-(pyridin-2-ylsulfonyl)cyclohexanecarboxamide | 43 |
| 9 | (1R*,3R*)-N-(5-isopropoxypyridin-2-yl)-3-(pyridin-4-ylsulfonyl)cyclohexanecarboxamide | 131 |
| 10 | (1R*,3R*)-N-(5-isopropoxypyridin-2-yl)-3-(pyrimidin-2-ylsulfonyl)cyclohexanecarboxamide | 26 |
| 11 | (1R*,3R*)-N-(5-isopropoxypyridin-2-yl)-3-(1,3-thiazol-2-ylsulfonyl)cyclohexanecarboxamide | 32 |
| 13 | (1R*,3R*)-N-(5-isopropoxypyridin-2-yl)-3-(pyrazin-2-ylsulfonyl)cyclohexanecarboxamide | 130 |

The compounds of the invention can be administered orally or parenterally, and after formulated into preparations suitable to such administration modes, the compounds can be used as preventives or remedies, for example, for circular system disorders such as hypertension, stenocardia, heart failure, myocardial infarction, stroke, claudication, diabetic nephropathy, diabetic retinopathy, reduced vision, electrolytic abnormality, atherosclerosis, etc.; central nervous system disorders such as bulimia, diabetic neuropathy, etc.; metabolic disorders such as metabolic syndrome, obesity, diabetes, insulin resistance, hyperlipidemia, hypercholesterolemia, hypertriglyceridemia, dyslipidemia, non-alcoholic fatty liver, hormone secretion abnormality, gout, fatty liver, etc.; reproduction system disorders such as menstrual abnormality, sexual dysfunction, etc.; digestive system disorders such as hepatic dysfunction, pancreatitis, cholecystitis, gastroesophageal reflux, etc.; respiratory system disorders such as obesity hypoventilation syndrome (Pickwickian syndrome), sleep apnea syndrome, etc.; infectious disorders caused by bacteria, fungi, parasites; malignant neoplasm; inflammatory disorders such as arthritis, skin ulcer, etc.

Another aspect of the invention is to provide a therapeutical method or a preventive method for disorders, diseases or conditions caused by LCE dysmodulation, which comprises administering a therapeutically or preventively effective amount of a compound of the invention to a subject in need thereof.

Still another aspect of the invention is to provide a therapeutical method or a preventive method for metabolic syndrome, fatty liver, hyperlipidemia, dyslipidemia, non-alcoholic fatty liver, obesity, diabetes, bulimia, malignant neoplasm or infectious disorders, which comprises administering a therapeutically or preventively effective amount of a compound of the invention to a subject in need thereof.

Still another aspect of the invention is to provide a therapeutical method or a preventive method for diabetes, which comprises administering a therapeutically or preventively effective amount of a compound of the invention to a subject in need thereof.

Still another aspect of the invention is to provide a therapeutical method or a preventive method for obesity, which comprises administering a therapeutically or preventively effective amount of a compound of the invention to a subject in need thereof.

Still another aspect of the invention is to provide a therapeutical method or a preventive method for obesity-related disorders selected from overeating, bulimia, hypertension, plasma insulin increase, insulin resistance, hyperlipidemia, endometrial cancer, breast cancer, prostate cancer, colon cancer, renal cancer, osteoarthritis, obstructive sleep apnea syndrome, heart disease, abnormal heartbeat rhythm, cardiac arrhythmia, myocardial infarction, congestive heart failure, coronary artery heart disease, sudden death, stroke, polycystic ovary, craniopharyngioma, metabolic syndrome, insulin resistance syndrome, sexual function and reproduction function failure, infertility, hypogonadism, hirsutism, obesity-related gastroesophageal reflux, obesity hypoventilation syndrome (Pickwickian syndrome), inflammations, systemic vasculitis, atherosclerosis, hypercholesterolemia, hyperuricemia, low back pain, inflammations, systemic vasculitis, atherosclerosis, hypercholesterolemia, hyperuricemia, low back pain, gallbladder disease, gout, constipation, inflammatory bowel syndrome, irritable bowel syndrome, heart hypertrophy and left ventricular dilatation, which method comprises administering a therapeutically or preventively effective amount of a compound of the invention to a subject in need thereof.

Still another aspect of the invention is to provide a therapeutical method or a preventive method for hyperlipidemia or dyslipidemia, which comprises administering a therapeutically or preventively effective amount of a compound of the invention to a subject in need thereof.

Still another aspect of the invention is to provide a method of calorie intake, which comprises administering a therapeutically or preventively effective amount of a compound of the invention to a subject in need thereof.

Still another aspect of the invention is to provide a method of reducing food intake, which comprises administering a therapeutically or preventively effective amount of a compound of the invention to a subject in need thereof.

Still another aspect of the invention is to provide a method of increasing satiety, which comprises administering a therapeutically or preventively effective amount of a compound of the invention to a subject in need thereof.

Still another aspect of the invention is to provide a method of appetite reduction, which comprises administering a therapeutically or preventively effective amount of a compound of the invention to a subject in need thereof.

The invention also relates to a therapeutical method or a preventive method for obesity, which comprises administering a compound of the invention as combined with a therapeutically or preventively effective amount of any other drug known useful for therapy or prevention for the condition.

The invention also relates to a therapeutical method or a preventive method for diabetes, which comprises administering a compound of the invention as combined with a therapeutically or preventively effective amount of any other drug known useful for therapy or prevention for the condition.

Still another aspect of the invention is to provide a pharmaceutical composition containing a compound of the invention and a pharmaceutically-acceptable carrier.

Still another aspect of the invention relates to use of a compound of the invention for production of medicaments useful for remedy, prevention or inhibition of LCE-caused disorders for subjects in need thereof.

Still another aspect of the invention relates to use of a compound of the invention for production of medicaments useful for remedy or prevention for metabolic syndrome, hyperlipidemia, dyslipidemia, non-alcoholic fatty liver, obesity, diabetes, bulimia, malignant neoplasm or infectious disorders for subjects in need thereof.

Still another aspect of the invention relates to use of a compound of the invention for production of medicaments useful for remedy or prevention for obesity for subjects in need thereof.

Still another aspect of the invention relates to use of a compound of the invention for production of medicaments useful for remedy or prevention for diabetes for subjects in need thereof.

Still another aspect of the invention relates to use of a compound of the invention for production of medicaments useful for remedy or prevention for hyperlipidemia or dyslipidemia for subjects in need thereof.

Still another aspect of the invention relates to use of a therapeutically effective amount of a compound of the invention and a therapeutically-effective amount of a drug or a pharmaceutically-acceptable salt thereof selected from a group consisting of insulin resistance relievers, insulin analogues, sulfonylureas, α-glucosidase inhibitors, dipeptidylpeptidase 4 (DPP-4 or DP-IV) inhibitors, glucagon-like peptide 1 (GLP-1) agonists, HMG-CoA reductase inhibitors, serotonin-like substances, β3-adrenalin receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanin concentration hormone receptor agonists, melanocortin 4 receptor agonists, bombesin receptor sub-type 3 agonists, ghrelin antagonists, PYY, $PYY_{3-36}$ and NK-1 antagonists, which is for use for production of medicines useful for therapy, control and prevention for obesity, diabetes, diabetes-related disorders or obesity-related disorders for subjects in need thereof.

Still another aspect of the invention relates to use of a therapeutically effective amount of a compound of the invention and a therapeutically-effective amount of a drug or a pharmaceutically-acceptable salt thereof selected from a group consisting of insulin resistance relievers, insulin analogues, sulfonylureas, α-glucosidase inhibitors, dipeptidylpeptidase 4 (DPP-4 or DP-IV) inhibitors, glucagon-like peptide 1 (GLP-1) agonists, HMG-CoA reductase inhibitors, serotonin-like substances, β3-adrenalin receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanin concentration hormone receptor agonists, melanocortin 4 receptor agonists, bombesin receptor sub-type 3 agonists, ghrelin antagonists, PYY, $PYY_{3-36}$ and NK-1 antagonists, which is for use for production of medicines useful for therapy or prevention for obesity, diabetes, diabetes-related disorders or obesity-related disorders and wherein an effective amount of the compound of the invention and an effective amount of the above-mentioned drug are used at the same time or at different times.

Still another aspect of the invention relates to a product as a combination of a therapeutically effective amount of a compound of the invention and a therapeutically-effective amount of a drug or a pharmaceutically-acceptable salt thereof selected from a group consisting of insulin resistance relievers, insulin analogues, sulfonylureas, α-glucosidase inhibitors, dipeptidylpeptidase 4 (DPP-4 or DP-IV) inhibitors, glucagon-like peptide 1 (GLP-1) agonists, HMG-CoA reductase inhibitors, serotonin-like substances, β3-adrenalin receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanin concentration hormone receptor agonists, melanocortin 4 receptor agonists, bombesin receptor sub-type 3 agonists, ghrelin antagonists, PYY, $PYY_{3-36}$ and NK-1 antagonists, which is for simultaneous, separate or continuous use thereof for obesity, diabetes, diabetes-related disorders or obesity-related disorders.

Still another aspect of the invention relates to use of a therapeutically effective amount of a compound of the invention and a therapeutically-effective amount of a drug or pharmaceutically-acceptable salt thereof selected from a group consisting of simvastatin, mevastatin, ezetimibe, atorvastatin, sitagliptin, metformin, sibutramine, orlistat, Qnexa (trade name) and phentermine, which is for use for production of medicaments useful for remedy, control or prevention for obesity, diabetes, diabetes-related disorders or obesity-related disorders for subjects in need thereof.

In clinical use of the compounds of the invention, pharmaceutically-acceptable additives may be added thereto, and after formulated into preparations suitable to their administration modes, the preparations can be administered. As the additives, usable are various additives generally used in the field of pharmaceutical preparations. For example, they include gelatin, lactose, white sugar, titanium oxide, starch, crystalline cellulose, methylated cellulose, hydroxypropylmethyl cellulose, carboxymethyl cellulose, corn starch, microcrystalline wax, white vaseline, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic anhydride, talc, vegetable oil, benzyl alcohol, gum arabic, propylene glycol, polyalkylene glycol, cyclodextrin, hydroxypropylcyclodextrin, etc.

The preparations to be formulated as a mixture with the additive include, for example, solid preparations such as tablets, capsules, granules, powders, suppositories; and liquid preparations such as syrups, elixirs, injections. These can be prepared according to ordinary methods in the filed of pharmaceutical preparations. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals and plants including humans and other mammals that require treatment with the compound. The mammals are preferably humans and may be men or women. Example of mammals other than humans include, for example, companion animals such as dogs, cats. The compounds of the invention are effective for obesity and obesity-related disorders of those dogs, cats, etc. Ordinary physicians, veterinarians and clinicians may readily determine the necessity of treatment with a compound of the invention.

In the case of using the compound of the invention for, e.g., a clinical purpose, the dose and administration frequency may vary depending on the sex, age, body weight, conditions of the patient, the type and range of the required treatment using the compound, and so on. In oral administration, the dose of the compound may be from 0.01 to 100 mg/kg of adult/day (preferably from 0.03 to 1 mg/kg of adult/day) and the administration frequency is preferably from one to several times. In parenteral administration, the dose may be from 0.001 to 10 mg/kg of adult/day (preferably from 0.001 to 0.1 mg/kg of adult/day, more preferably from 0.01 to 0.1 mg/kg of adult/day) and the administration frequency is preferably from one to several times.

For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient, since the dose is to be adjusted depending on the conditions of the patient to be treated. The compounds may be administered on a regimen of 1 to 4 times per day, preferably once or twice per day.

In the case of using the compounds of the invention for treating or preventing obesity and/or diabetes and/or hyperlipemia and/or dyslipidemia and/or non-alcoholic fatty liver or other diseases, satisfactory results can be generally obtained by administering the compounds of the invention in a daily dosage of from about 0.1 mg to about 100 mg per kilogram of animal body weight, preferably in a single daily dose or in divided doses two to six times a day, or as sustained release preparations. In the case of many large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic effects.

Ordinary physicians, veterinarians and clinicians may readily determine and apply an effective dose necessary for treating, preventing, inhibiting, suppressing or stopping the development of diseases.

The preparation may contain a compound of the invention in a ratio of from 1.0 to 100% by weight, preferably from 1.0 to 60% by weight of all the ingredients constituting it. The preparation may also contain any other therapeutically-effective compound.

The compounds of the invention may be used as combined with any other agent useful for treatment of diseases, for example, circular system disorders such as hypertension, stenocardia, heart failure, myocardial infarction, stroke, claudication, diabetic nephropathy, diabetic retinopathy, reduced vision, electrolytic abnormality, atherosclerosis, etc.; central nervous system disorders such as bulimia, diabetic neuropathy, etc.; metabolic disorders such as metabolic syndrome, obesity, diabetes, insulin resistance, hyperlipidemia, hypercholesterolemia, hypertriglyceridemia, dyslipidemia, non-alcoholic fatty liver, hormone secretion abnormality, gout, fatty liver, etc.; reproduction system disorders such as menstrual abnormality, sexual dysfunction, etc.; digestive system disorders such as hepatic dysfunction, pancreatitis, cholecystitis, gastroesophageal reflux, etc.; respiratory system disorders such as obesity hypoventilation syndrome (Pickwickian syndrome), sleep apnea syndrome, etc.; infectious disorders caused by bacteria, fungi, parasites; malignant neoplasm; inflammatory disorders such as arthritis, skin ulcer, etc. The individual ingredients of those combinations may be administered at different times or at the same time during the period of treatment, as divided preparations or as a single preparation. Accordingly, the invention should be interpreted to encompass all administration modes at the same time or at different times, and the administration in the invention should be interpreted so. The scope of the combination of the compound of the invention and the other agent useful for the above-mentioned diseases encompasses, in principle, any and every combination with any and every pharmaceutical preparation useful for the above-mentioned diseases.

The above-mentioned combination includes not only a composition of the invention containing only one other active substance but also a combination containing 2 or more other active substances. There are many examples of the combinations of the composition of the invention with one or more active substances selected from the remedial medicines for the above-mentioned diseases. For example, for the purpose of treatment, control and prevention for metabolic syndrome, the composition of the invention may be combined effectively with 1 or more active substances selected from remedies for hyperlipidemia, lipid lowering agent and anti-diabetics. In particular, a composition containing an anti-obesity drug or an anti-hypertension drug in addition to an anti-diabetes drug and/or a remedy for hyperlipidemia or a lipid lowering agent exhibits a synergistic effect for treatment, control or prevention of metabolic syndrome.

The drugs that may be combined with the composition of the invention include, for example, ACAT inhibitors, α-blockers, aldose reductase inhibitors, α-amylase inhibitors, angiotensin converting enzyme inhibitors, angiotensin receptor antagonists, anion exchange resins, anorectics, antioxidants, antiplatelet drugs, β-blockers, biguanide agents, calcium antagonists, CB1 receptor inverse agonists/antagonists, CETP inhibitors, cholesterol absorption inhibitors, DGAT inhibitors, DP-IV inhibitors, diuretics, eicosapentaenoic acid, endothelin inhibitors, FLAP inhibitors, FXR modulators, ghrelin antagonists, GLP-1 agonists, GLP-1 secretory agents, glucagon antagonists, glucokinase activators, glucocorticoid receptor ligands, α-glucosidase inhibitors, GPAT inhibitors, histamine H3 receptor ligands, HMG-CoA reductase inhibitors, HSD inhibitors, insulin and its analogues, kinase inhibitors such as VEGF inhibitors/PDFG inhibitors, reptin, lipase inhibitors, 5-LO inhibitors, LXR ligands, melanocortin agonists, MCH antagonists, MTTP inhibitors, olexin antagonists, opioid antagonists, neuropeptide Y antagonists, nicotinic acid agonists, PPAR ligands, PTP-1B inhibitors, SCD-1 inhibitors, serotonin transporter inhibitors, SGLT inhibitors, SUR ligands, thyroid hormone agonists, UCP activators, VPAC receptor agonists, etc.

ADVANTAGES OF THE INVENTION

The compounds of the invention have an excellent LCE-inhibitory effect, and are useful as remedies for LCE-related various diseases, for example, circular system disorders, nervous system disorders, metabolic disorders, reproduction system disorders, digestive system disorders, neoplasm, infectious diseases, etc., or as herbicides.

BEST MODE FOR CARRYING OUT THE INVENTION

The invention is described more concretely with reference to Reference Examples and Examples given below, by which, however, the invention should not be limited at all.

EXAMPLES

In thin-layer chromatography, Silica $Gel_{60}F_{254}$ (Merck) was used for the plate, and a UV detector was used for detection. Wakogel™ C-300 or C-200 (Wako Pure Chemical Industries), FLASH+Cartridge (Biotage) or Chromatorex (Fuji Silysia Chemical) was used for column silica gel. In MS spectrometry, used was ZQ2000 (Waters). In NMR spectrometry, dimethylsulfoxide was used as the internal standard in a heavy dimethylsulfoxide solution; a spectrometer of JNM- AL 400 (JEOL), Mercury 400 (400 MHz; Varian) or Inova 400 (400 MHz; Varian) was used; and all δ values are shown by ppm.

The meanings of the abbreviations in NMR analysis are mentioned below.

s: singlet
d: doublet
dd: double doublet
t: triplet
dt: double triplet
q: quartet
m: multiplet
br: broad
J: coupling constant
Hz: hertz
DMSO-$d_6$: heavy dimethylsulfoxide
(1R*,3R*) means a 1/1 mixture of (1R,3R) and (1S,3S); and (1R*,3S*) means a 1/1 mixture of (1R,3S) and (1S,3R).

Example 1

(1R*,3R*)-N-(4-isopropoxyphenyl)-3-(phenylsulfonyl)cyclohexanecarboxamide, and (1R*,3S*)-N-(4-isopropoxyphenyl)-3-(phenylsulfonyl)cyclohexanecarboxamide

[Chemical Formula 9]

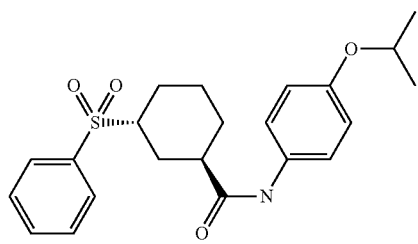

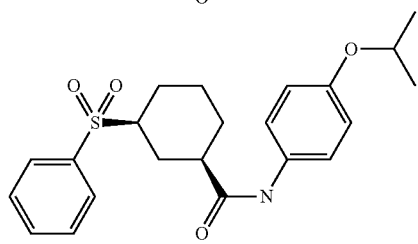

(1) Production of N-(4-isopropoxyphenyl)-3-(phenylthio)cyclohexanecarboxamide

Potassium carbonate (149 mg, 1.078 mmol) and potassium iodide (179 mg, 1.078 mmol) were added to a DMF (3 mL) solution of the entitled compound (85 mg, 0.239 mmol) in Reference Example 1 and thiophenol (119 mg, 1.078 mmol), and stirred at 80° C. for 24 hours. This was restored to room temperature, then ethyl acetate was added thereto, and washed three times with distilled water. The organic layer was dried with magnesium sulfate, and concentrated under reduced pressure. The resulting residue was purified through silica gel column chromatography to give the intended product (56 mg, 64%).

(2) Production of the Entitled Compound

M-chloroperbenzoic acid (69% concentration) (83 mg, 0.332 mmol) was added to a chloroform (2 mL) solution of the compound (49 mg, 0.133 mmol) obtained in the above (1), and stirred at room temperature for 5 hours. Aqueous saturated sodium thiosulfate solution was added thereto and stirred for a while. The organic layer was washed twice with aqueous saturated sodium bicarbonate solution, dried with magnesium sulfate, and concentrated under reduced pressure. The resulting residue was purified through silica gel column chromatography to give (1R*,3R*)-N-(4-isopropoxyphenyl)-3-(phenylsulfonyl)cyclohexanecarboxamide (21.4 mg, 40%), and (1R*,3S*)-N-(4-isopropoxyphenyl)-3-(phenylsulfonyl)cyclohexanecarboxamide (1.9 mg, 3.5%).

(1R*,3R*)-N-(4-isopropoxyphenyl)-3-(phenylsulfonyl)cyclohexanecarboxamide $^1$H-NMR (400 MHz, CDCl$_3$, δ): 1.31 (6H, d, J=6.3 Hz), 1.67-1.78 (3H, m), 1.83-1.99 (4H, m), 2.20-2.29 (1H, m), 2.84-2.93 (1H, m), 3.61-3.72 (1H, m), 4.42-4.54 (1H, m), 6.80-6.86 (2H, m), 7.21 (1H, s), 7.31-7.36 (2H, m), 7.53-7.59 (2H, m), 7.62-7.68 (1H, m), 7.88-7.92 (2H, m).
ESI-MS (m/z): 402.2 [M+H]$^+$ (1R*,3S*)-N-(4-isopropoxyphenyl)-3-(phenylsulfonyl)cyclohexanecarboxamide $^1$H-NMR (400 MHz, CDCl$_3$, δ): 1.31 (6H, d, J=6.3 Hz), 1.67-1.78 (3H, m), 1.83-1.99 (4H, m), 2.20-2.29 (1H, m), 2.84-2.93 (1H, m), 3.61-3.72 (1H, m), 4.42-4.54 (1H, m), 6.80-6.86 (2H, m), 7.21 (1H, s), 7.31-7.36 (2H, m), 7.53-7.59 (2H, m), 7.62-7.68 (1H, m), 7.88-7.92 (2H, m).
ESI-MS (m/z): 402.1 [M+H]$^+$ Example 2

(1R*,3R*)-N-(4-isopropoxyphenyl)-3-(pyridin-2-ylsulfonyl)cyclohexanecarboxamide

[Chemical Formula 10]

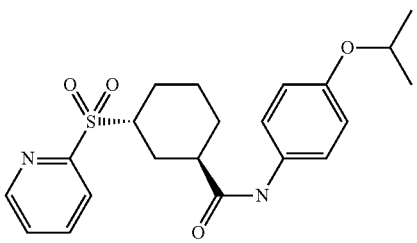

(1) Production of (1R*,3R*)-N-(4-isopropoxyphenyl)-3-(pyridin-2-ylthio)cyclohexanecarboxamide The entitled compound was produced according to the method of Example 1(1) but using the entitled compound in Reference Example 1 and 2-mercaptopyridine.

(2) Production of the Entitled Compound

The entitled compound was produced according to the method of Example 1(2) but using the compound produce in the above (1).

$^1$H-NMR (400 MHz, CDCl$_3$, δ): 1.29-1.33 (6H, m), 1.68-1.78 (1H, m), 1.80-2.01 (5H, m), 2.09-2.18 (1H, m), 2.20-2.29 (1H, m), 2.86-2.98 (1H, m), 4.06-4.17 (1H, m), 4.42-

4.55 (1H, m), 6.78-6.89 (2H, m), 7.18-7.22 (1H, m), 7.33-7.42 (2H, m), 7.51-7.59 (1H, m), 7.94-8.00 (1H, m), 8.09-8.14 (1H, m), 8.73-8.78 (1H, m).

ESI-MS (m/z): 403.2 [M+H]$^+$

Example 3

(1R*,3R*)-N-(4-isopropoxyphenyl)-3-(pyrimidin-2-ylsulfonyl)cyclohexanecarboxamide

[Chemical Formula 11]

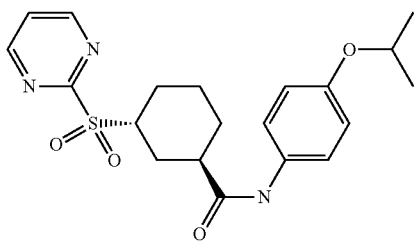

The entitled compound was produced according to the method of Example 2 but using the entitled compound in Reference Example 1 and 2-mercaptopyrimidine.

$^1$H-NMR (400 MHz, CDCl$_3$, δ): 1.31 (6H, d, J=6.3 Hz), 1.73-1.80 (1H, m), 1.83-1.89 (2H, m), 1.90-2.02 (2H, m), 2.04-2.20 (2H, m), 2.24-2.34 (1H, m), 2.90-2.99 (1H, m), 4.31-4.39 (1H, m), 4.43-4.54 (1H, m), 6.79-6.88 (2H, m), 7.30-7.41 (3H, m), 7.53-7.59 (1H, m), 8.93-8.99 (2H, m).

ESI-MS (m/z): 404.0 [M+H]$^+$

Example 4

(1R*,3R*)-N-(4-isopropoxyphenyl)-3-(1,3-thiazol-2-ylsulfonyl)cyclohexanecarboxamide

[Chemical Formula 12]

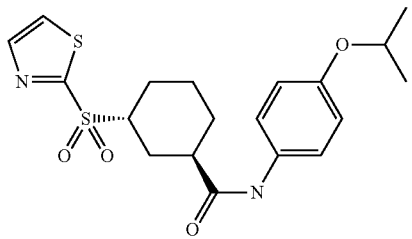

The entitled compound was produced according to the method of Example 2 but using the entitled compound in Reference Example 1 and 2-mercaptothiazole.

$^1$H-NMR (400 MHz, CDCl$_3$, δ): 1.31 (6H, d, J=5.9 Hz), 1.71-1.79 (1H, m), 1.80-1.94 (3H, m), 1.95-2.08 (2H, m), 2.10-2.18 (1H, m), 2.31-2.40 (1H, m), 2.88-2.95 (1H, m), 4.00-4.10 (1H, m), 4.43-4.54 (1H, m), 6.80-6.86 (2H, m), 7.33-7.39 (2H, m), 7.72-7.76 (1H, m), 8.03-8.08 (1H, m)

ESI-MS (m/z): 409.0 [M+H]$^+$.

Example 5

(1R*,3R*)-N-(4-isopropoxyphenyl)-3-(1,3,4-thiadiazol-2-ylsulfonyl)cyclohexanecarboxamide

[Chemical Formula 13]

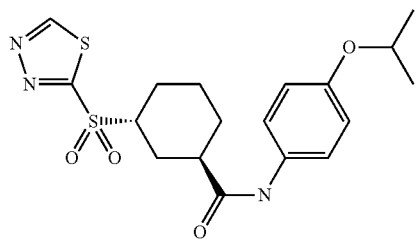

The entitled compound was produced according to the method of Example 2 but using the entitled compound in Reference Example 1 and 2-mercapto-1,3,4-thiadiazole.

$^1$H-NMR (400 MHz, CDCl$_3$, δ): 1.27 (7H, d, J=6.3 Hz), 1.68-1.80 (2H, m), 1.83-1.98 (3H, m), 2.07-2.18 (2H, m), 2.39-2.48 (1H, m), 2.83-2.91 (1H, m), 4.16-4.25 (1H, m), 4.41-4.51 (1H, m), 6.76-6.85 (2H, m), 7.24-7.28 (1H, m), 7.30-7.37 (2H, m), 9.35-9.37 (1H, m).

ESI-MS (m/z): 410.0 [M+H]$^+$

Example 6

(1R*,3R*)-N-(4-isopropoxyphenyl)-3-[(1-methyl-1H-imidazol-2-yl)sulfonyl]cyclohexanecarboxamide

[Chemical Formula 14]

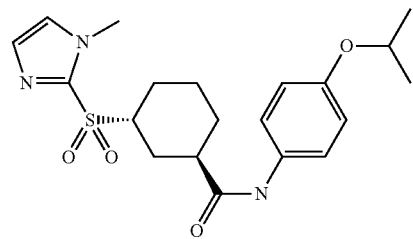

The entitled compound was produced according to the method of Example 2 but using the entitled compound in Reference Example 1 and 2-mercapto-1-methylimidazole.

$^1$H-NMR (400 MHz, CDCl$_3$, δ): 1.31 (6H, d, J=5.9 Hz), 1.59-1.80 (2H, m), 1.82-1.96 (2H, m), 2.04-2.18 (3H, m), 2.38-2.51 (1H, m), 2.89-2.98 (1H, m), 3.94-4.04 (4H, m), 4.44-4.55 (1H, m), 6.81-6.88 (2H, m), 7.01-7.06 (1H, m), 7.12-7.16 (1H, m), 7.41-7.47 (2H, m), 7.98-8.07 (1H, m).

ESI-MS (m/z): 406.0 [M+H]$^+$

Example 7

(1R*,3R*)-N-(5-isopropoxypyridin-2-yl)-3-(phenyl-sulfonyl)cyclohexanecarboxamide

[Chemical Formula 15]

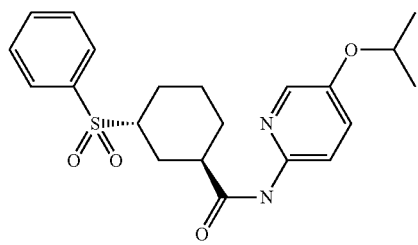

(1) Production of (1R*,3R*)-N-(5-isopropoxypyridin-2-yl)-3-(phenylthio)cyclohexanecarboxamide The entitled compound was produced according to the method of Example 2(1) but using the entitled compound in Reference Example 2 and thiophenol.

(2) Production of the Entitled Compound

Acetic acid (30.5 μL, 0.535 mmol) and potassium permanganate (50.5 mg, 0.321 mmol) were added to a mixed solution of the compound (39.5 mg, 0.107 mmol) produced in the above (1) in acetone (0.75 mL)/distilled water (0.75 mL), and stirred at room temperature for 19 hours. Most of the reaction solution was concentrated under reduced pressure, and chloroform and aqueous saturated sodium bicarbonate solution were added to the residue, and extracted three times with chloroform. The organic layer was collected, dried with magnesium sulfate, and concentrated under reduced pressure. The resulting residue was purified through silica gel column chromatography to give the entitled compound (19 mg, 44%).

$^1$H-NMR (400 MHz, CDCl$_3$, δ): 1.33 (6H, d, J=6.3 Hz), 1.55-1.79 (3H, m), 1.81-2.00 (4H, m), 2.24-2.33 (1H, m), 2.87-2.95 (1H, m), 3.65-3.74 (1H, m), 4.45-4.56 (1H, m), 7.20-7.25 (1H, m), 7.53-7.59 (2H, m), 7.62-7.68 (1H, m), 7.88-7.93 (3H, m), 7.96-8.00 (1H, m), 8.01-8.07 (1H, m).
ESI-MS (m/z): 403.0 [M+H]$^+$

Example 8

(1R*,3R*)-N-(5-isopropoxypyridin-2-yl)-3-(pyridin-2-ylsulfonyl)cyclohexanecarboxamide

[Chemical Formula 16]

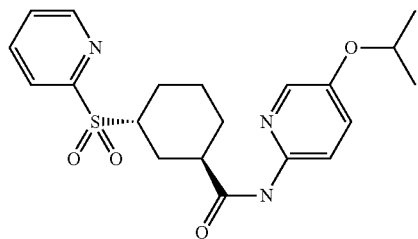

The entitled compound was produced according to the method of Example 7 but using the entitled compound in Reference Example 2 and 2-mercaptopyridine.

$^1$H-NMR (400 MHz, CDCl$_3$, δ): 1.33 (6H, d, J=5.9 Hz), 1.63-1.74 (1H, m), 1.78-1.99 (5H, m), 2.01-2.11 (1H, m), 2.21-2.31 (1H, m), 2.91-3.01 (1H, m), 4.10-4.20 (1H, m), 4.46-4.56 (1H, m), 7.21-7.25 (1H, m), 7.52-7.59 (1H, m), 7.91-8.03 (3H, m), 8.05-8.14 (2H, m), 8.77-8.82 (1H, m).
ESI-MS (m/z): 404.0 [M+H]$^+$

Example 9

(1R*,3R*)-N-(5-isopropoxypyridin-2-yl)-3-(pyridin-4-ylsulfonyl)cyclohexanecarboxamide

[Chemical Formula 17]

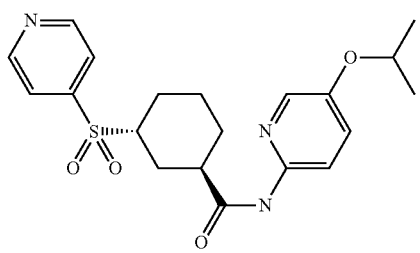

The entitled compound was produced according to the method of Example 7 but using the entitled compound in Reference Example 2 and 4-mercaptopyridine.

$^1$H-NMR (400 MHz, CDCl$_3$, δ): 1.33 (6H, d, J=6.3 Hz), 1.55-1.78 (3H, m), 1.80-1.89 (2H, m), 1.90-2.05 (2H, m), 2.23-2.31 (1H, m), 2.86-2.95 (1H, m), 3.78-3.88 (1H, m), 4.44-4.56 (1H, m), 7.21-7.25 (1H, m), 7.76-7.80 (2H, m), 7.90-7.93 (1H, m), 7.99-8.06 (2H, m), 8.88-8.95 (2H, m).
ESI-MS (m/z): 404.0 [M+H]$^+$

Example 10

(1R*,3R*)-N-(5-isopropoxypyridin-2-yl)-3-(pyrimidin-2-ylsulfonyl)cyclohexanecarboxamide

[Chemical Formula 18]

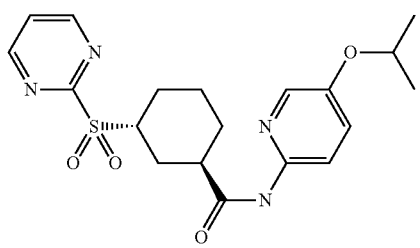

The entitled compound was produced according to the method of Example 7 but using the entitled compound in Reference Example 2 and 2-mercaptopyrimidine.

$^1$H-NMR (400 MHz, CDCl$_3$, δ): 1.34 (6H, d, J=6.3 Hz), 1.67-1.75 (1H, m), 1.77-1.87 (1H, m), 1.90-2.04 (3H, m), 2.06-2.18 (2H, m), 2.34-2.43 (1H, m), 2.94-3.05 (1H, m), 4.30-4.40 (1H, m), 4.45-4.56 (1H, m), 7.21-7.28 (1H, m), 7.54-7.61 (1H, m), 7.91-7.96 (1H, m), 8.08-8.18 (2H, m), 8.99-9.05 (2H, m)
ESI-MS (m/z): 405.0 [M+H]$^+$.

Example 11

(1R*,3R*)-N-(5-isopropoxypyridin-2-yl)-3-(1,3-thiazol-2-ylsulfonyl)cyclohexanecarboxamide

[Chemical Formula 19]

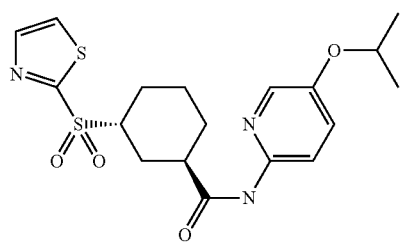

The entitled compound was produced according to the method of Example 7 but using the entitled compound in Reference Example 2 and 2-mercaptothiazole.

$^1$H-NMR (400 MHz, CDCl$_3$, δ): 1.33 (6H, d, J=6.3 Hz), 1.65-1.97 (5H, m), 2.03-2.13 (2H, m), 2.34-2.44 (1H, m), 2.91-2.99 (1H, m), 4.04-4.13 (1H, m), 4.46-4.56 (1H, m), 7.21-7.25 (1H, m), 7.73-7.77 (1H, m), 7.91-7.94 (1H, m), 8.01-8.10 (3H, m).

ESI-MS (m/z): 410.0 [M+H]$^+$

Example 12

(1R*,3R*)-3-(butylsulfonyl)-N-(5-isopropoxypyridin-2-yl)cyclohexanecarboxamide

[Chemical Formula 20]

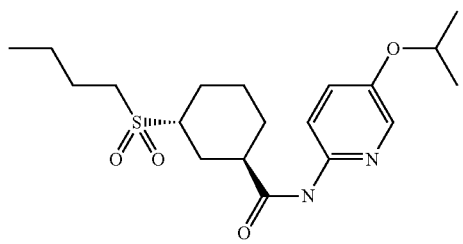

The entitled compound was produced according to the method of Example 7 but using the entitled compound in Reference Example 2 and 1-butanethiol.

$^1$H-NMR (400 MHz, CDCl$_3$, δ): 0.88 (3H, t, J=7.3 Hz), 1.33 (6H, d, J=6.3 Hz), 1.35-1.46 (2H, m), 1.50-1.61 (1H, m), 1.63-1.84 (4H, m), 1.86-2.07 (3H, m), 2.15-2.26 (1H, m), 2.89-3.07 (2H, m), 3.13-3.26 (2H, m), 4.46-4.56 (1H, m), 7.19-7.25 (1H, m), 7.93-7.99 (1H, m), 8.03-8.09 (1H, m), 8.36-8.44 (1H, m).

ESI-MS (m/z): 383.0 [M+H]$^+$

Example 13

(1R*,3R*)-N-(5-isopropoxypyridin-2-yl)-3-(pyrazin-2-ylsulfonyl)cyclohexanecarboxamide

[Chemical Formula 21]

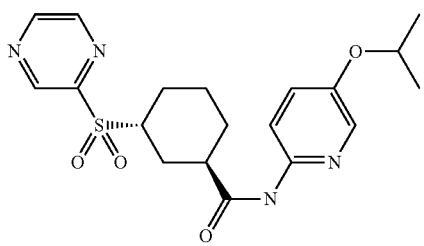

(1) Production of (1R*,3R*)-N-(5-isopropoxypyridin-2-yl)-3-(pyrazin-2-ylthio)cyclohexanecarboxamide The entitled compound (60 mg, 0.168 mmol) in Reference Example 2, 2-mercaptopyrazine (113 mg, 1.010 mmol) and cesium carbonate (329 mg, 1.010 mmol) were stirred in DMF (1 mL) at 80° C. for 5 hours. The temperature of the reaction system was restored to room temperature, then ethyl acetate was added to it, and washed twice with distilled water and once with saturated brine. The organic layer was dried with magnesium sulfate, and concentrated under reduced pressure. The resulting residue was purified through silica gel column chromatography to give the intended product.

(2) Production of the Entitled Compound

The entitled compound was produced according to the method of Example 7(2) but using the compound produced in the above (1).

$^1$H-NMR (400 MHz, CDCl$_3$, δ): 1.34 (6H, d, J=5.9 Hz), 1.62-1.75 (1H, m), 1.77-1.95 (4H, m), 1.98-2.07 (2H, m), 2.26-2.35 (1H, m), 2.92-3.01 (1H, m), 4.08-4.24 (1H, m), 4.45-4.57 (1H, m), 7.21-7.26 (1H, m), 7.90-7.96 (1H, m), 8.02-8.12 (2H, m), 8.76-8.81 (1H, m), 8.85-8.90 (1H, m), 9.29-9.34 (1H, m).

ESI-MS (m/z): 405.2 [M+H]$^+$

Example 14

(1R*,3R*)-N-(3-isopropoxy-1H-pyrazol-5-yl)-3-(pyridin-2-ylsulfonyl)cyclohexanecarboxamide, and (1R*,3S*)-N-(3-isopropoxy-1H-pyrazol-5-yl)-3-(pyridin-2-ylsulfonyl)cyclohexanecarboxamide

[Chemical Formula 22]

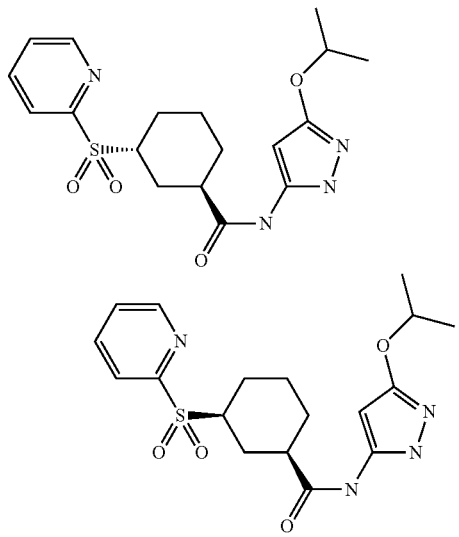

1-(3-Dimethylaminopropyl)-3-ethylcarbodiimide hydrochloride (hereinafter abbreviated as EDC) (144 mg, 0.752 mmol) was added to a pyridine (5 mL) solution of the entitled compound (184 mg, 0.683 mmol) in Reference Example 3 and 3-amino-5-isopropoxy-1H-pyrazole (101 mg, 0.717 mmol), and stirred at room temperature for 24 hours. The reaction solution was concentrated under reduced pressure, then ethyl acetate was added thereto, and washed once with aqueous 1 N sodium hydroxide solution and once with saturated brine. The organic layer was dried with magnesium sulfate, and concentrated under reduced pressure. The resulting residue was purified through silica gel column chromatography to give (1R*,3R*)-N-(3-isopropoxy-1H-pyrazol-5-yl)-3-(pyridin-2-ylsulfonyl)cyclohexanecarboxamide (5.7 mg, 2.1%), and (1R*,3S*)-N-(3-isopropoxy-1H-pyrazol-5-yl)-3-(pyridin-2-ylsulfonyl)cyclohexanecarboxamide (3.1 mg, 1.1%).

(1R*,3R*)-N-(3-isopropoxy-1H-pyrazol-5-yl)-3-(pyridin-2-ylsulfonyl)cyclohexanecarboxamide $^1$H-NMR (400 MHz, CDCl$_3$, δ): 1.31-1.38 (6H, m), 1.65-1.78 (2H, m), 1.79-2.02 (3H, m), 2.13-2.20 (2H, m), 2.22-2.31 (1H, m), 3.06-3.17 (1H, m), 4.04-4.11 (1H, m), 5.94 (1H, s), 7.54-7.63 (1H, m), 7.94-8.01 (1H, m), 8.07-8.15 (1H, m), 8.74-8.80 (1H, m), 10.09 (1H, br s).
ESI-MS (m/z): 393.2 [M+H]$^+$ (1R*,3S*)-N-(3-isopropoxy-1H-pyrazol-5-yl)-3-(pyridin-2-ylsulfonyl)cyclohexanecarboxamide $^1$H-NMR (400 MHz, CDCl$_3$, δ): 1.34 (7H, d, J=6.3 Hz), 1.39-1.64 (3H, m), 1.76-1.88 (1H, m), 1.92-2.07 (2H, m), 2.10-2.17 (1H, m), 2.19-2.37 (2H, m), 3.52-3.66 (1H, m), 4.55-4.66 (1H, m), 5.65 (1H, s), 7.55-7.61 (1H, m), 7.94-8.02 (1H, m), 8.08-8.14 (1H, m), 8.41 (1H, br s), 8.74-8.80 (1H, m).
ESI-MS (m/z): 393.2 [M+H]$^+$

Example 15

N-(4-isopropoxyphenyl)-3-(phenylsulfonyl)piperidine-1-carboxamide

[Chemical Formula 23]

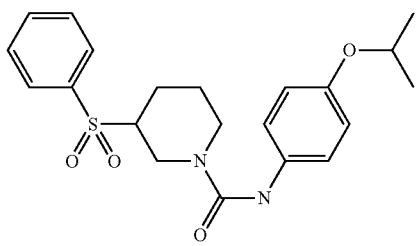

(1) Production of benzyl 3-(phenylthio)piperidine-1-carboxylate

The entitled compound was produced according to the method of Example 1(1) but using benzyl 3-[(methylsulfonyl)oxy]piperidine-1-carboxylate produced according to the method described in a known reference (WO96/39407) and thiophenol.

(2) Production of benzyl 3-(phenylsulfonyl)piperidine-1-carboxylate

The entitled compound was produced according to the method of Example 1(2) but using benzyl 3-(phenylthio)piperidine-1-carboxylate produced in the above (1).

(3) Production of 3-(phenylsulfonyl)piperidine

10% Palladium-carbon catalyst (40 mg) was added to a methanol (2 mL) solution of the compound (84 mg, 0.234 mmol) produced in the above (2), and stirred in the presence of hydrogen at room temperature for 18 hours. The reaction liquid was filtered through Celite, and the filtrate was concentrated. The resulting residue was dissolved in ethyl acetate, then washed once with aqueous 1 N sodium hydroxide solution and once with saturated brine. The organic layer was dried with magnesium sulfate and concentrated under reduced pressure to give the intended product (43 mg, 82%).

(4) Production of the Entitled Compound

Triethylamine (0.08 mL, 0.573 mmol) and phenyl (4-isopropoxyphenyl)carbamate (67.3 mg, 0.248 mmol) were added to a chloroform (3 mL) solution of the compound (43 mg, 0.191 mmol) produced in the above (3), and stirred at 80° C. for 24 hours. The reaction system was restored to room temperature, and washed once with aqueous 1 N sodium hydroxide solution and once with saturated brine. The organic layer was dried with magnesium sulfate, and concentrated under reduced pressure. The resulting residue was purified through silica gel column chromatography to give the entitled compound (45.7 mg, 59%).

¹H-NMR (400 MHz, CDCl₃, δ): 1.30 (6H, d, J=5.9 Hz), 1.49-1.61 (1H, m), 1.77-1.93 (2H, m), 2.16-2.25 (1H, m), 2.88-2.98 (1H, m), 3.06-3.20 (2H, m), 3.82-3.89 (1H, m), 4.27-4.34 (1H, m), 4.43-4.51 (1H, m), 6.31 (1H, br s), 6.78-6.84 (2H, m), 7.13-7.19 (2H, m), 7.55-7.63 (2H, m), 7.66-7.72 (1H, m), 7.86-7.94 (2H, m).

ESI-MS (m/z): 403.3 [M+H]⁺

Reference Example 1

3-{[(4-isopropoxyphenyl)amino]carbonyl}cyclohexyl methanesulfonate

[Chemical Formula 24]

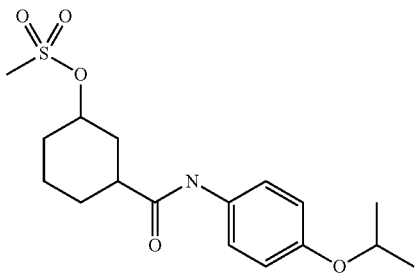

(1) Production of N-(4-isopropoxyphenyl)-3-oxocyclohexanecarboxamide

4-Isopropoxyaniline (117 mg, 0.774 mmol), HATU (294 mg, 0.774 mmol) and diisopropylethylamine (0.27 mL, 1.548 mmol) were added in that order to a DMF (3 mL) solution of 3-oxo-1-cyclohexanecarboxylic acid (100 mg, 0.703 mmol), and stirred at room temperature for 5 hours. Ethyl acetate was added to the reaction liquid, and washed with distilled water and saturated brine. The organic layer was dried with magnesium sulfate, and concentrated under reduced pressure. The residue was purified through silica gel column chromatography to give the intended product (194 mg, 100%).

(3) Production of 3-hydroxy-N-(4-isopropoxyphenyl)cyclohexanecarboxamide

With cooling with ice, sodium borohydride (28.9 mg, 0.763 mmol) was added to a methanol (6 mL) solution of the compound (175 mg, 0.636 mmol) produced in the above (1), and stirred for a while, and then further stirred at room temperature for 3 hours. Aqueous saturated ammonium chloride solution was added to it, stirred for a while, and the reaction solvent was concentrated under reduced pressure. Distilled water was added to the resulting residue, and extracted twice with chloroform. The organic layer was collected, dried with magnesium sulfate, and concentrated under reduced pressure. The residue was purified through silica gel column chromatography to give the intended product (162 mg, 92%).

(3) Production of the Entitled Compound

Triethylamine (0.098 mmol, 0.7 mmol) and methanesulfonyl chloride (0.05 mL, 0.642 mmol) were added in that order to a chloroform (5 mL) solution of the compound (162 mg, 0.584 mmol) obtained in the above (2), and stirred for 24 hours. The reaction solution was washed once with distilled water, dried with magnesium sulfate, and under reduced pressure. The resulting residue was purified through silica gel column chromatography to give the entitled compound (179 mg, 86%) as a cis/trans mixture.

Reference Example 2

3-{[(5-isopropoxypyridin-2-yl)amino]carbonyl}cyclohexyl methanesulfonate

[Chemical Formula 25]

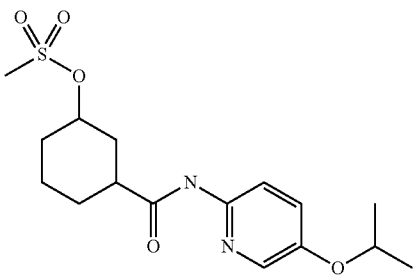

(1) Production of 2-bromo-5-isopropoxypyridine

2-Bromopropane (1.13 mL, 12 mmol) and potassium carbonate (1.43 g, 10.4 mmol) were added in that order to a DMF (10 mL) solution of 6-bromopyridin-3-ol (1 g, 5.75 mmol), and stirred at 80° C. for 2 hours. The temperature of the solution was restored to room temperature, then this was diluted with ethyl acetate, washed twice with distilled water and once with saturated brine. The organic layer was dried with magnesium sulfate and concentrated under reduced pressure to give the intended product (1.28 g, 100%).

(2) Production of ethyl 5-isopropoxypyridine-2-carboxylate

Palladium acetate (31.3 mg, 0.14 mol) and 1,1'-bis(diphenylphosphino)ferrocene (77.1 mg, 0.14 mmol) were added to a mixed solution of the compound (600 mg, 2.78 mmol) obtained in the above (1) in ethanol (6 mL) and DMF (3 mL), and stirred in the presence of carbon monoxide at 50° C. for 22 hours. The reaction solution was diluted with ethyl acetate, and washed twice with aqueous saturated sodium bicarbonate solution and once with saturated brine. The resulting organic layer was dried with magnesium sulfate and concentrated under reduced pressure. The resulting residue was purified through silica gel column chromatography to give the intended product (386 mg, 66%).

(3) Production of 5-isopropoxypyridine-2-carboxylic acid

Aqueous 5 N sodium hydroxide solution (1.8 mL) was added to an ethanol (3 mL) solution of the compound (386 mg, 1.84 mmol) obtained in the above (2), and stirred at 50° C. for 3 hours. The reaction liquid was cooled with ice, neutralized with aqueous 5 N hydrochloric acid solution, and the reaction liquid was extracted with chloroform. The organic layer was collected, dried with magnesium sulfate, and concentrated under reduced pressure to give the intended product (258 mg, 78%).

(4) Production of tert-butyl (5-isopropoxypyridin-2-yl)carbamate

Triethylamine (0.585 mL, 4.2 mmol) and diphenylphosphoric acid azide (0.453 mL, 2.1 mmol) were added in that order to a tert-butanol (5 mL) solution of the compound (255 mg, 1.4 mmol) obtained in the above (3), and stirred at 100° C. for 5 hours. The reaction liquid was restored to room temperature, and concentrated under reduced pressure. The residue was dissolved in ethyl acetate, washed twice with aqueous 1 N sodium hydroxide solution and once with saturated brine. The organic layer was dried with magnesium sulfate, and concentrated under reduced pressure. The resulting residue was purified through silica gel column chromatography to give the intended product (137 mg, 39%).

(5) Production of 2-amino-5-isopropoxypyridine hydrochloride

4 N hydrochloric acid/ethyl acetate solution (4.5 mL) was added to a chloroform (5 mL) solution of the compound (137 mg, 0.54 mmol) obtained in the above (4), and stirred at room temperature for 18 hours. The reaction solution was concentrated under reduced pressure to give the intended product (102 mg, 100%).

(6) Production of the Entitled Compound

The entitled compound was produced according to the method of Reference Example 1 but using the compound obtained in the above (5) as the starting material.

Reference Example 3

(1R*,3R*)-3-(pyridin-2-ylsulfonyl)cyclohexanecarboxylic acid

[Chemical Formula 26]

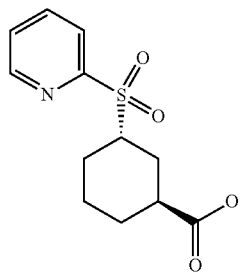

(1) Production of methyl (1S*,3R*)-3-[(methylsulfonyl)oxy]cyclohexanecarboxylate With cooling with ice, triethylamine (1.51 mL, 10.84 mol) and mesyl chloride (0.643 mL, 8.13 mmol) were added in that order to an ethyl acetate (10 mL) solution of a compound, methyl (1S*,3R*)-3-hydroxycyclohexanecarboxylic acid (857 mg, 5.42 mmol) known in a reference (Tetrahedron, 2003, Vol. 59, pp. 7465-7471), and then stirred at room temperature for 1 hour. The reaction solution was kept under cooling with ice for while, and then the reaction liquid was filtered. The resulting filtrate was concentrated under reduced pressure to give the intended product (1.18 g, 92%).

(2) Production of methyl (1R*,3R*)-3-(pyridin-2-ylthio)cyclohexanecarboxylate 2-Mercaptopyridine (847 mg, 7.62 mmol) and cesium carbonate (2.48 g, 7.62 mmol) were added in that order to a DMF (5 mL) solution of the compound (300 mg, 1.27 mmol) produced in the above (1), and stirred at 80° C. for 4 hours. The reaction solution was restored to room temperature, diluted with ethyl acetate, and washed twice with distilled water and once with saturated brine. The organic layer was dried with magnesium sulfate, and concentrated under reduced pressure. The resulting residue was purified through silica gel column chromatography to give the intended product (252 mg, 79%).

(3) Production of methyl (1R*,3R*)-3-(pyridin-2-ylsulfonyl)cyclohexanecarboxylate M-chloroperbenzoic acid (622 mg (69% concentration), 2.49 mmol) was added to a chloroform (5 mL) solution of the compound (250 mg, 0.995 mmol) produced in the above (2), and stirred at room temperature for 24 hours. Aqueous saturated sodium thiosulfate solution was added to it, stirred for a while, and extracted twice with chloroform. The organic layer was collected, dried with magnesium sulfate, and concentrated under reduced pressure. The resulting residue was purified through silica gel column chromatography to give the intended product (240 mg, 85%).

(4) Production of the Entitled Compound

Aqueous 5 N sodium hydroxide solution (0.847 mL) was added to a methanol (5 mL) solution of the compound (240 mg, 0.847 mmol) produced in the above (3), and stirred at room temperature for 14 hours. The reaction solution was cooled with ice, and neutralized with aqueous 5 N hydrochloric acid solution. This was extracted three times with chloroform. The organic layer was collected, dried with magnesium sulfate, and concentrated under reduced pressure to give the entitled compound (210 mg, 92%).

INDUSTRIAL APPLICABILITY

The compounds of the invention have an excellent LCE-inhibitory effect, and are useful as remedies for LCE-related various diseases, for example, circular system disorders, nervous system disorders, metabolic disorders, reproduction system disorders and digestive system disorders, or as herbicides.

The invention claimed is:

1. A compound of a formula (I) or a pharmaceutically-acceptable salt thereof:

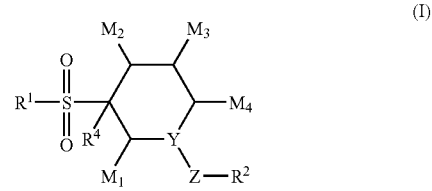

wherein,

Z is (II-1):

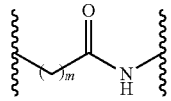

m indicates 0, 1 or 2;

Y represents $CR^3$;

$R^1$ represents methyl, ethyl, propyl, butyl, cyclopropyl, phenyl, 2-pyridyl, 3-pyridyl, 4-pyridyl, 2-methoxyphenyl, pyrimidin-2-yl, 3-methoxyphenyl, 4-methoxyphenyl, 2-fluorophenyl, 3-fluorophenyl, 4-fluorophenyl, 2-chlorophenyl, 3 chlorophenyl, 4-chlorophenyl, 1-methyl-1H-imidazole-4-yl, 1H-imidazole-4-yl, 5-methyl-1,3,4-thiadiazol-2-yl or 1,3,4-thiadiazol-2-yl;

$R^2$ represents phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2-isopropylphenyl, 3-isopropylphenyl, 4-isopropylphenyl, 2-isopropoxyphenyl, 3-isopropoxyphenyl, 4-isopropoxyphenyl, 2-benzylphenyl, 3-benzylphenyl, 4-benzylphenyl, 2-benzyloxyphenyl, 3-benzyloxyphenyl, 4-benzyloxyphenyl, 5-isopropoxyphenylpyridin-2-yl, 6-isopropoxyphenylpyridin-3-yl, 5-isopropoxypyrimidin-2-yl, 3-methoxypyridin-2-yl, 3-cyclopropyl-1H-pyrazol-5-yl or 5-isopropoxy-1H-pyrazol-3-yl;

$R^3$ and $R^4$ each independently represent a hydrogen atom; $M_1$, $M_2$, $M_3$ and $M_4$ each independently represent a hydrogen atom.

2. The compound or the pharmaceutically-acceptable salt thereof as claimed in claim 1, wherein Z is represented by a formula (II-1), and m is 0 or 1.

3. The compound or the pharmaceutically-acceptable salt thereof as claimed in claim 1, wherein the compound of formula (I) is selected from a group consisting of the following:

3R)—N-(5-isopropoxypyridin-2-yl)-3-(phenylsulfonyl)cyclohexanecarboxamide, (1R,3R)—N-(5-isopropoxypyridin-2-yl)-3-(pyridin-2-ylsulfonyl)cyclohexanecarboxamide, (1R,3R)—N-(5-isopropoxypyridin-2-yl)-3-(pyrimidin-2-ylsulfonyl)cyclohexanecarboxamide, (1R,3R)—N-(5-isopropoxypyridin-2-yl)-3-(1,3-thiazol-2-ylsulfonyl)cyclohexanecarboxamide, and (1R,3R)—N-(3-isopropoxy-1H-pyrazol-5-yl)-3-(pyridin-2-ylsulfonyl)cyclohexanecarboxamide.

4. A pharmaceutical composition containing a compound or a pharmaceutically-acceptable salt thereof of claim 1.

* * * * *